United States Patent
Li

(10) Patent No.: US 12,264,219 B2
(45) Date of Patent: Apr. 1, 2025

(54) CONDUCTIVE BENZOIC ACID BASED POLYMER CONTAINING BIOMATERIAL FOR ENHANCEMENT OF TISSUE CONDUCTION IN VITRO AND IN VIVO

(71) Applicant: UNIVERSITY HEALTH NETWORK, Toronto (CA)

(72) Inventor: Ren-Ke Li, Toronto (CA)

(73) Assignee: University Health Network, Toronto (CA)

(*) Notice: Subject to any disclaimer, the term of this patent is extended or adjusted under 35 U.S.C. 154(b) by 1108 days.

(21) Appl. No.: 16/634,026

(22) PCT Filed: Jul. 27, 2018

(86) PCT No.: PCT/CA2018/050914
§ 371 (c)(1),
(2) Date: Jan. 24, 2020

(87) PCT Pub. No.: WO2019/018942
PCT Pub. Date: Jan. 31, 2019

(65) Prior Publication Data
US 2021/0087336 A1 Mar. 25, 2021

Related U.S. Application Data

(60) Provisional application No. 62/537,755, filed on Jul. 27, 2017.

(51) Int. Cl.
| | |
|---|---|
| *C08G 69/48* | (2006.01) |
| *A61L 31/04* | (2006.01) |
| *A61L 31/06* | (2006.01) |
| *A61L 31/14* | (2006.01) |
| *A61L 31/16* | (2006.01) |
| *A61N 1/05* | (2006.01) |
| *A61N 1/375* | (2006.01) |
| *C08L 89/06* | (2006.01) |

(52) U.S. Cl.
CPC ............ *C08G 69/48* (2013.01); *A61L 31/045* (2013.01); *A61L 31/06* (2013.01); *A61L 31/145* (2013.01); *A61L 31/16* (2013.01); *A61N 1/056* (2013.01); *A61N 1/37512* (2017.08); *C08L 89/06* (2013.01)

(58) Field of Classification Search
CPC ........ C08G 69/48; C08G 69/08; C08G 69/46; A61L 31/145; A61L 31/06; A61L 31/16; A61L 31/045; A61N 1/056; A61N 1/37512; A61K 9/0019; A61K 9/06; A61K 47/42; A61K 47/34; A61K 47/36; C08L 5/00; C08L 77/00; C08L 89/00; C08L 2203/02; C08L 2203/00; C08L 89/06; C08H 1/06; A61P 9/00
See application file for complete search history.

(56) References Cited

U.S. PATENT DOCUMENTS

| | | | |
|---|---|---|---|
| 9,289,533 B2 | 3/2016 | Schussler et al. | |
| 2006/0173058 A1* | 8/2006 | Brown | A61P 9/10 564/123 |
| 2015/0366900 A1* | 12/2015 | Li | A61L 27/26 526/258 |
| 2016/0032047 A1* | 2/2016 | Murphy | A61L 27/18 424/78.02 |

FOREIGN PATENT DOCUMENTS

| | | |
|---|---|---|
| WO | 2014121378 A1 | 8/2014 |
| WO | 2015025958 A1 | 2/2015 |

OTHER PUBLICATIONS

Encyclopedia of Polymeric Nanoparticles (Kensuke Naka (2014) pp. 1-6) (Year: 2014).*
Cingolani, E. et al. Engineered electrical conduction tract restores conduction in complete heart block: from in vitro to in vivo proof of concept. J Am Coll Cardiol. Dec. 23, 2014;64(24):2575-85.
Etsadashvili, K. et al. Long-term results of high vs. normal impedance ventricular leads on actual (Real-Life) pacemaker generator longevity. Eur Eur Pacing Arrhythm Card Electrophysiol J Work Groups Card Pacing Arrhythm Card Cell Electrophysiol Eur Soc Cardiol. Feb. 2009;11(2):200-5.
Ra, Li. Gene- and cell-based bio-artificial pacemaker: what basic and translational lessons have we learned? Gene Ther. Jun. 2012;19(6):588-95.
Miake, J. et al. Biological pacemaker created by gene transfer. Nature. Sep. 12, 2002;419(6903):132-3.
Tse, H-F. et al. Bioartificial sinus node constructed via in vivo gene transfer of an engineered pacemaker HCN Channel reduces the dependence on electronic pacemaker in a sick-sinus syndrome model. Circulation. Sep. 5, 2006;114(10):1000-11.
Xue, T. et al. Mechanistic role of I(f) revealed by induction of ventricular automaticity by somatic gene transfer of gating-engineered pacemaker (HCN) channels. Circulation. Apr. 10, 2007;115(14):1839-50.
Choi, Y-H. et al. Cardiac conduction through engineered tissue. Am J Pathol. Jul. 2006;169(1):72-85.
Mulpuru, S. K. et al. Cardiac Pacemakers: Function, Troubleshooting, and Management: Part 1 of a 2-Part Series. J Am Coll Cardiol. Jan. 17, 2017;69(2):189-210.
Mcvenes, R. et al. The salty dog: serum sodium and potassium effects on modern pacing electrodes. Pacing Clin Electrophysiol PACE. Jan. 2007;30(1):4-11. (Abstract).

(Continued)

*Primary Examiner* — Anna R Falkowitz
(74) *Attorney, Agent, or Firm* — Smart & Biggar LP; Carmela De Luca

(57) ABSTRACT

The present disclosure relates to a biocompatible, electrically conductive biomaterial capable of carrying the electrical potential of a cardiac impulse. The biomaterial comprises a conductive polymer and a biocompatible component. The conductive polymer comprising an aminomethoxybenzoic acid (AMBA) polymer. The present disclosure also relates to treatments, uses and devices using the biocompatible, electrically conductive biomaterial.

18 Claims, 25 Drawing Sheets

(56) References Cited

OTHER PUBLICATIONS

Lee, R. J. et al. Development of a model of complete heart block in rats. J Appl Physiol Bethesda Md 1985. Aug. 1998;85(2):758-63.
Dai, W. et al. Thickening of the infarcted wall by collagen injection improves left ventricular function in rats: a novel approach to preserve cardiac function after myocardial infarction. J Am Coll Cardiol. Aug. 16, 2005;46(4):714-9.
Ifkovits, J. L. et al. Injectable hydrogel properties influence infarct expansion and extent of postinfarction left ventricular remodeling in an ovine model. Proc Natl Acad Sci U S A. Jun. 22, 2010;107(25):11507-12.
Christman, K. L. et al. Injectable fibrin scaffold improves cell transplant survival, reduces infarct expansion, and induces neovasculature formation in ischemic myocardium. J Am Coll Cardiol. Aug. 4, 2004;44(3):654-60.
Maccarter, D. J. et al. Porous electrodes: concept, technology and results. Pacing and clinical electrophysiology : PACE. 1983;6:427-435.
Herrlich, S. et al. Drug release mechanisms of steroid eluting rings in cardiac pacemaker lead electrodes. Conference proceedings : . . . Annual International Conference of the IEEE Engineering in Medicine and Biology Society. IEEE Engineering in Medicine and Biology Society. Annual Conference. 2012;2012:681-684.
Elmqvist, H. et al. The carbon tip electrode. Pacing and clinical electrophysiology : PACE. 1983;6:436-439.
Echave, M. C. et al. Gelatin as Biomaterial for Tissue Engineering. Current pharmaceutical design. 2017. (Abstract).
Laughner, J. I. et al. Processing and analysis of cardiac optical mapping data obtained with potentiometric dyes. American journal of physiology. Heart and circulatory physiology. 2012;303:H753-765.
Curtis, M. J. et al. The Lambeth Conventions(II): guidelines for the study of animal and human ventricular and supraventricular arrhythmias. Pharmacol. Ther. 139, 213-248 (2013).
Nguyen, T. et al. Postinfarction survival and inducibility of ventricular arrhythmias in the spontaneous hypertensive rat: effects of ramipril and hydralazine. Circulation 98, 2074-2080 (1998).
Ortega, D. F. et al. Non-selective His bundle pacing with a biphasic waveform: enhancing septal resynchronization. Europace. 816-822. (2017).
Mond, H. et al. The high impedance dish electrode—clinical experience with a new tined lead. Pacing and clinical electrophysiology: PACE. 1982;5:529-534.
Masini, M. et al. Activated pyrolytic carbon tip pacing leads: an alternative to steroid-eluting pacing leads? Pacing and clinical electrophysiology: PACE. 1996;19:1832-1835.
Frohlig, G. et al. A fractally coated, 1.3 mm2 high impedance pacing electrode. Pacing and clinical electrophysiology: PACE. 1998;21:1239-1246.
Crossley, G. H. et al. Extraction of chronically implanted coronary sinus leads active fixation vs passive fixation leads. Heart Rhythm. 2016;13:1253-1259.
Mond, H. G. et al. The electrode-tissue interface: the revolutionary role of steroid-elution. Pacing and clinical electrophysiology: PACE. 2014;37:1232-1249.
Netusil, M. Small surface electrodes for cardiac pacing and their effect on the longevity of pacemakers. Cor et vasa. 1972;20:121-128. (Abstract).
Sideris, S. et al. Left Ventricular Pacing through Coronary Sinus Is Feasible and Safe for Patients with Prior Tricuspid Valve Intervention. Pacing and clinical electrophysiology: PACE. 2016;39:378-381.
Furman, S. et al. Pulse duration variation and electrode size as factors in pacemaker longevity. The Journal of thoracic and cardiovascular surgery. 1975;69:382-389. (Abstract).
Kubus, P. et al. Permanent epicardial pacing in children: long-term results and factors modifying outcome. Europace. 2012;14:509-514.
Zhang, H. et al. A flexible and implantable piezoelectric generator harvesting energy from the pulsation of ascending aorta: in vitro and in vivo studies. Nano Energy. 2015;12:296-304.
Stokes, K. B. et al. The mythology of threshold variations as a function of electrode surface area. Pacing and clinical electrophysiology: PACE. 1991;14:1748-1751.
Mawad, D. et al. A conducting polymer with enhanced electronic stability applied in cardiac models. Science Advances 2-11, e1601007, (2016).
Shin, S. R. et al. Carbon-Nanotube-Embedded Hydrogel Sheets for Engineering Cardiac Constructs and Bioactuators. ACS Nano 7, 2369-2380, (2013).
Solazzo, M. et al. The rationale and emergence of electroconductive biomaterial scaffolds in cardiac tissue engineering. APL Bioengineering 3, 041501, (2019).
Tanne, J. et al. Carboxylated or Aminated Polyaniline-Multiwalled Carbon Nanotubes Nanohybrids for Immobilization of Cellobiose Dehydrogenase on Gold Electrodes. Biosensors 4, 370-386, (2014).
Liu, Y. et al. Synthesis and characterization of novel biodegradable and electroactive hydrogel based on aniline oligoner and gelatin. Macromol. Biosci., Oct. 25, 2011 (Oct. 25, 2011), (2012), vol. 12, 241-250.
Huang, L. et al. Synthesis and characterization of electroactive and biodegradable ABA block copolymer of polylactide and aniline pentamer. Biomaterials, Jan. 10, 2007 (Jan. 10, 2007), vol. 28, 1741-1751.

\* cited by examiner

Conductivity $= 1/(2\pi DR)$

D is the distance between probes (mm)
R=V (mV)/I (mA).

A 3-Dimensional Gelfoam Patch

Gelfoam    AMBA+Gelfoam    AMBA-Gelfoam

Gelfoam Patch Conductivity
Two-point Probe Measurements

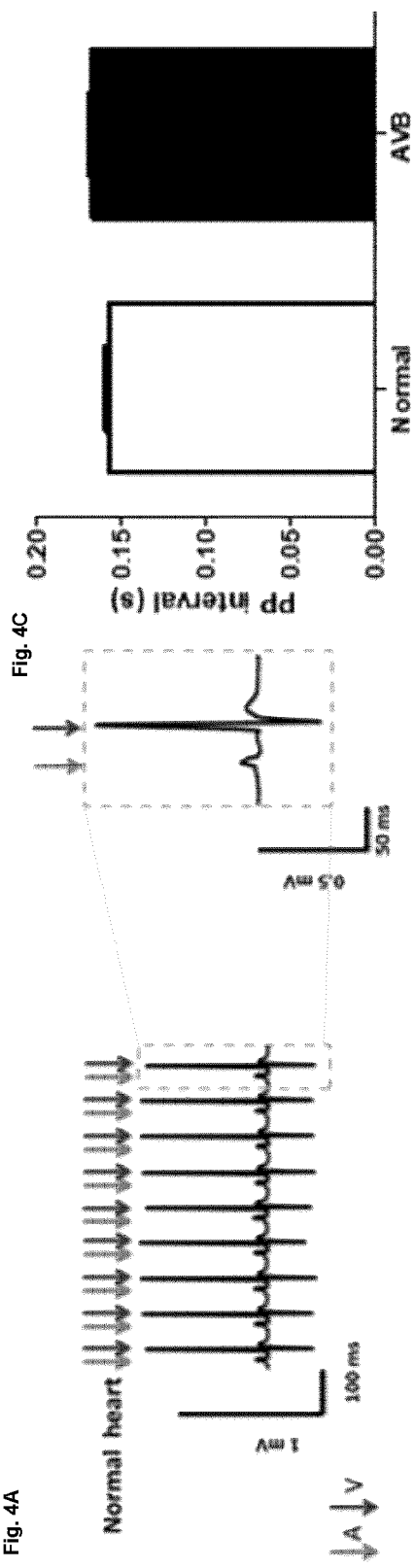
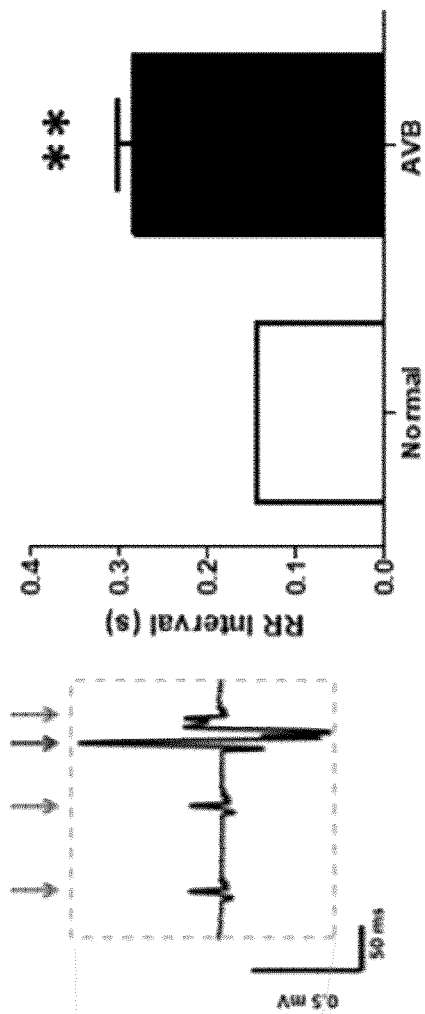

Gelatin

AMBA-Gelatin

Gelatin

AMBA-Gelatin

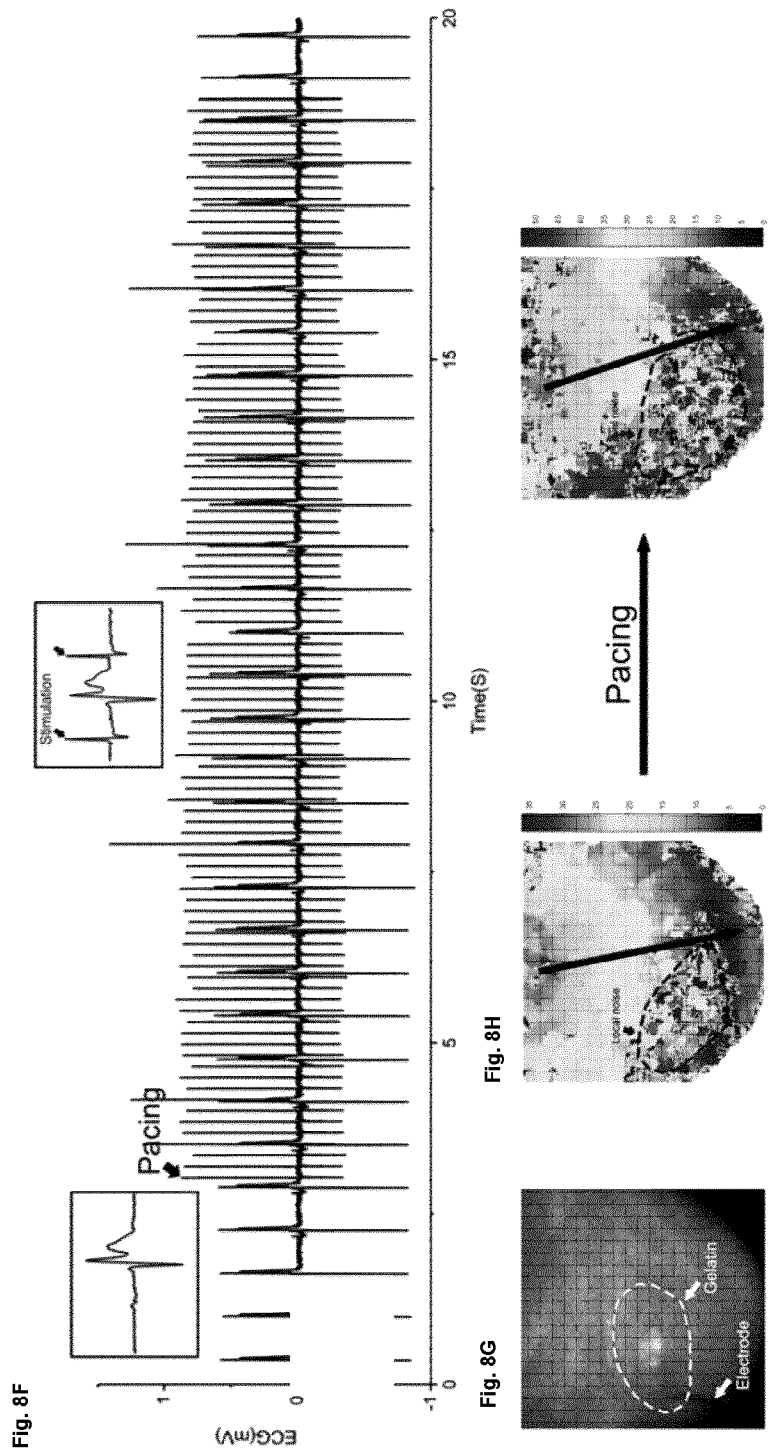

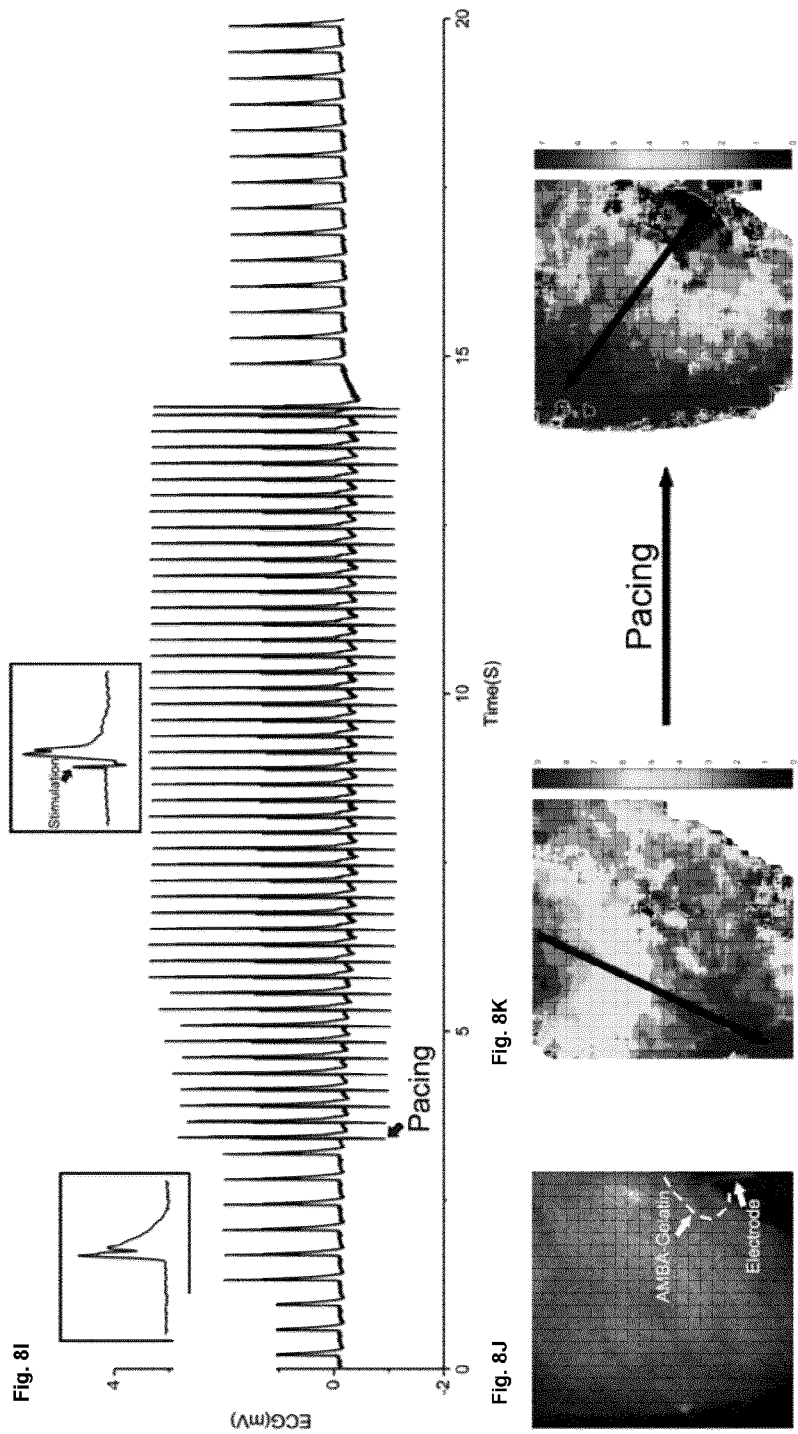

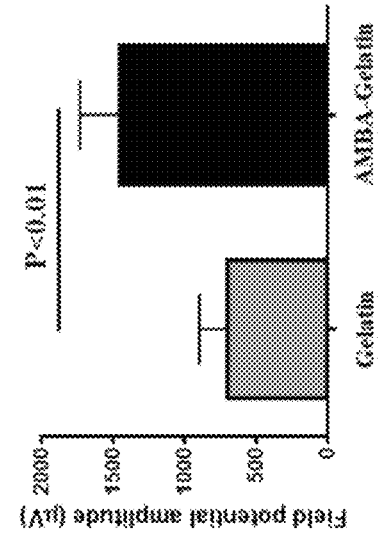
Fig. 13A
Fig. 13B
Fig. 13C
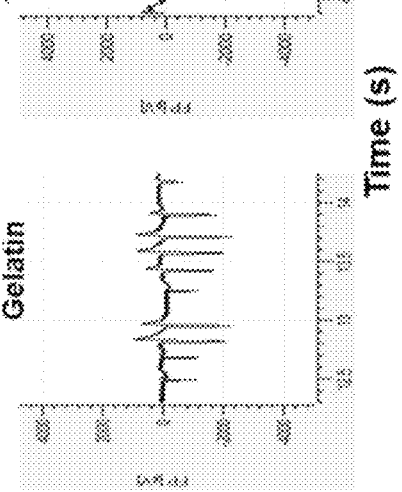
Fig. 13D
Fig. 13E
Fig. 13F
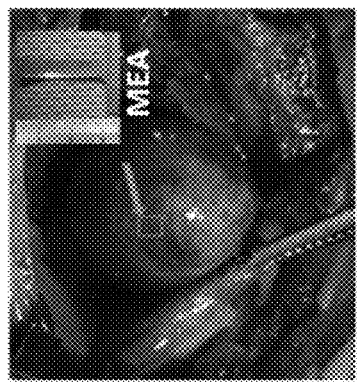
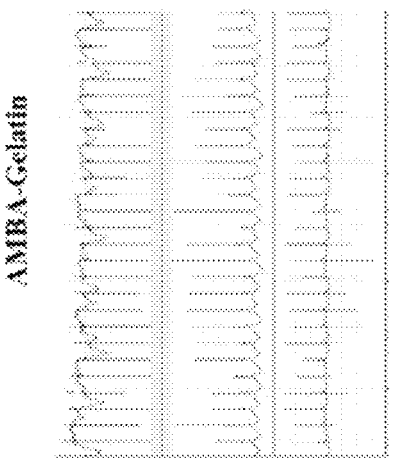
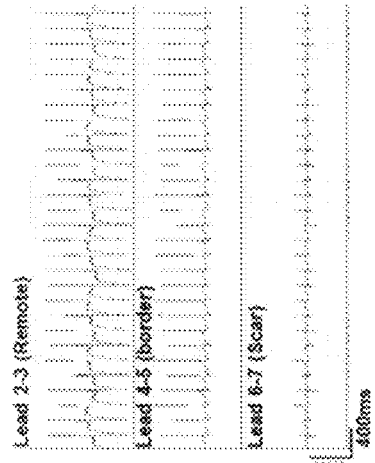
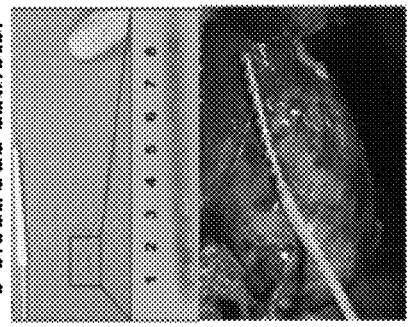

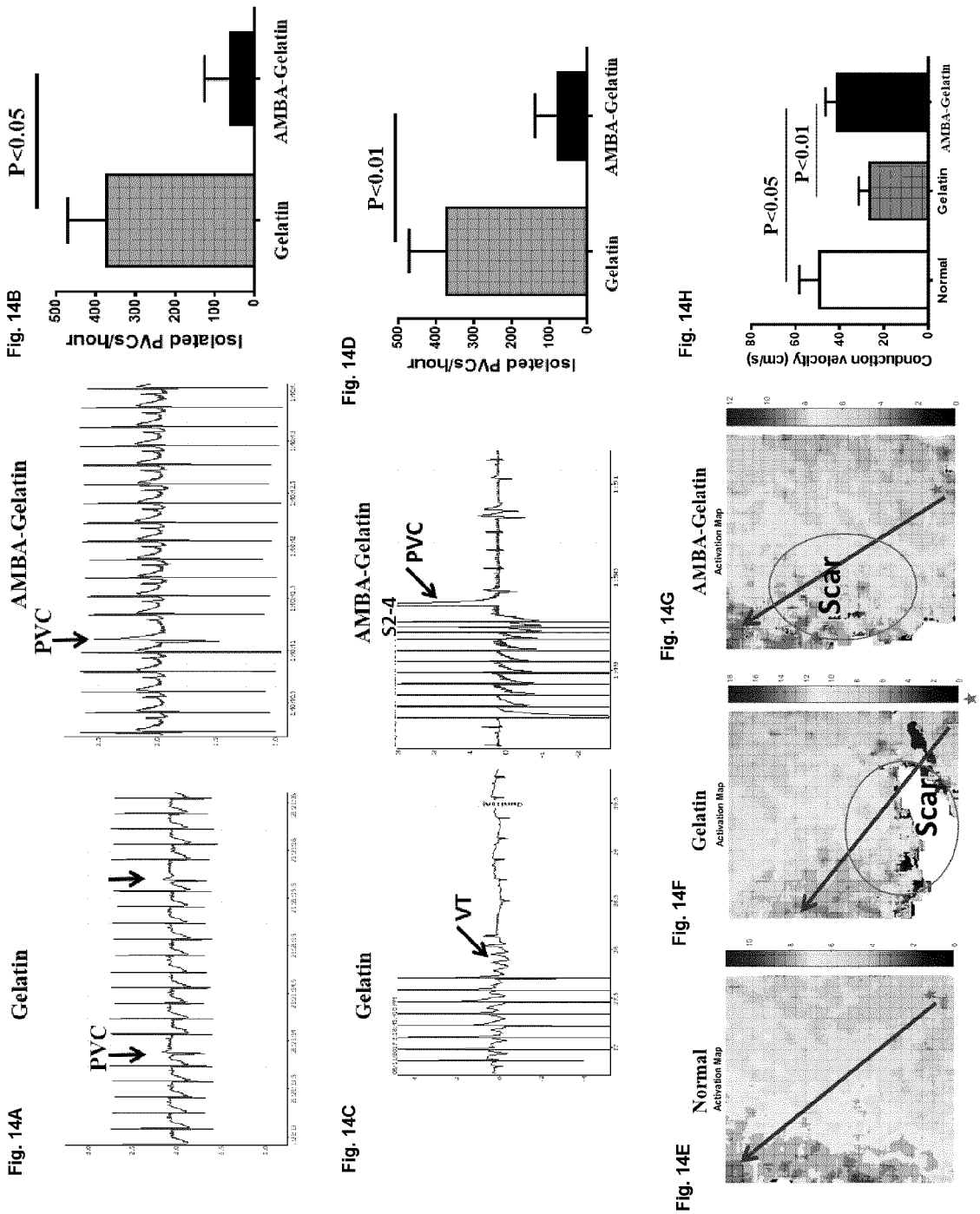

CONDUCTIVE BENZOIC ACID BASED POLYMER CONTAINING BIOMATERIAL FOR ENHANCEMENT OF TISSUE CONDUCTION IN VITRO AND IN VIVO

CROSS-REFERENCE TO RELATED APPLICATIONS

This application is a national phase entry of PCT/CA2018/050914, filed Jul. 27, 2018, which claims priority from U.S. Provisional patent application Ser. No. 62/537,755 filed Jul. 27, 2017; each of these applications being incorporated herein in their entirety by reference.

FIELD

The present disclosure relates to a biocompatible, electrically conductive biomaterial capable of carrying the electrical potential of a cardiac impulse. The present disclosure also relates to treatments using the electrically conductive biomaterial. The present disclosure also relates to devices using the electrically conductive biomaterial.

BACKGROUND

Cardiac electrical conduction delays and block, such as atrioventricular block (AVB), are associated with serious clinical conditions that increase the risk of life-threatening rhythm disturbances and heart failure [1]. Standard of care relies on electronic pacemakers to artificially restore synchrony. However, the mortality of cardiac sudden death is still a major clinical problem.

A permanent artificial pacemaker is the current treatment for AVB since the conduction system does not regenerate. It is also the current treatment for symptomatic bradycardia. While pacemakers have revolutionized patient survival and quality of life, their limitations are obvious, such as limited lifetime of the leads and power supplies [2].

Due to their limited lifetime, patients may need to receive a second operation to replace the exhausted pacemaker after the first implantation [2]. Pacemaker threshold is an important parameter related with energy consumption in cardiac pacemaker [8, 9], and any novel techniques which can reduce threshold are helpful for cardiac pacemaker energy saving.

A number of technologies have been developed to improve pacemaker function. Porous electrode tips were developed to reduce pacing thresholds [14]. Steroid-eluting tips reduce the inflammatory response and then decrease local fibrosis, resulting in lower stimulation thresholds [15]. Carbon tip electrodes were also used to reduce the pacing threshold [16]. These modifications are effective, but the battery life is still limited and additional techniques are required to further reduce the myocardial impedance and lower the threshold of the pacemaker stimulation.

In addition, the activation pattern provided by pacemakers is not physiological. Right ventricular pacing does not provide appropriate impulse propagation, and left ventricular pacing may not restore the normal sequence of ventricular contraction. Therefore, new therapeutic strategies are needed. In the past decade, various gene- and cell-based approaches have been pursued to produce a bio-artificial pacemaker as an alternative to electronic pacemakers [3]. Gene modifications have been used to convert quiescent cardiomyocytes into pacemaker cells to generate spontaneous, rhythmic electrical activity in the heart in vivo [4-6]. Choi et al, engineered a cell-seeded collagen patch that was implanted in rats between the right atrium and right ventricle after induction of an AVB. Optical mapping showed that a third of the engineered hearts had established electrical AV conduction, which disappeared when the implants were destroyed [7]. These research data suggested that new technology is needed to ensure synchronous contraction of the heart and electrical integration of the tissue-engineered biomaterials with the native myocardium as well as appropriately timed activation of contraction in response to stimulation.

Myocardial infarction is major clinical problem contributing to mortality and morbidity worldwide. Advanced medical therapy saves more than 80% patients after heart attack. However, most survivors have cardiac arrhythmia because of myocardial fibrosis followed by cardiomyocytes necrosis. The fibrotic tissue in the myocardium has great conductive resistance. Therefore, the uneven conduction between myocardial fibrotic tissue and normal myocardium results in fetal ventricular tachyarrhythmia via micro-reentry pathway leads to sudden cardiac death. Medication therapy has had limited effectiveness.

Conductive biomaterials are a class of organic biomaterials that transmit electricity. Their conductive properties can be enhanced electrochemically. Reversible oxidation of conductive polymers (such as polypyrrole, polyaniline, polythiophene, and poly 3-4-ethylenedioxythiophene) may increase their conductivity yet maintain redox stability. These conductive polymers are currently being evaluated for use as bio-probes, stimulation of nerve regeneration, controlled drug release, and artificial muscles.

In the past decades, a variety of biomaterials including fibrin, collagen and hyaluronic acid have been used to stabilize the infarct region and prevent or delay scar thinning and ventricular dilatation after MI [11-13]. Gene- and cell-based approaches have been pursued to produce a bio-artificial pacemaker as an alternative to electronic pacemakers [3-7]. However, none of these biomaterials are electrically conductive.

SUMMARY

The present disclosure relates to a biocompatible, electrically conductive biomaterial capable of treating heart conditions of conductive-related abnormalities including myocardial infarction and other heart related conditions.

In one embodiment, the present disclosure relates to a biocompatible conductive biomaterial comprising a conductive polymer and a biocompatible component. The conductive polymer can be polymerized with benzoic acids, such as aminomethoxybenzoic acids (AMBA). The biocompatible component can include a polysaccharide, protein or polypeptide, such as gelatin. The biocompatible conductive biomaterial can for example be incorporated into, or made into, a conductive hydrogel, membrane, 3D-patch or sponge, sheet, or mesh for grafting.

In another embodiment, the present disclosure relates to a method of treating a heart condition, the method comprising introducing a biocompatible conductive biomaterial to the heart, wherein the biomaterial comprises a conductive polymer and a biocompatible component. The heart condition can include myocardial infarction, ischemic myocardium, myocardial fibrosis, cardiac arrhythmia, heart failure, atrioventricular block (AVB), and/or other conduction abnormalities. The disclosure also relates to use of a biocompatible conductive biomaterial for treating a heart condition in an individual, wherein the biomaterial includes a conductive polymer and a biocompatible component.

In another embodiment, the present disclosure relates to a pacemaker device utilizing one of the biocompatible biomaterials described herein.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

For a better understanding of the embodiments described herein and to show more clearly how they may be carried into effect, reference will now be made, by way of example only, to the accompanying drawings which show at least one exemplary embodiment, and in which:

FIG. 4 shows Atrioventricular Block Rat (AVB) Model in vivo. (A) Representative raw surface ECG traces in normal rats. Each atrial wave "A" (identified with a grey arrow) was followed with a ventricular wave "V" (identified with a black arrow). (B) Representative raw surface ECG traces in AV block rats. Atrial wave "A" and ventricular wave "V" were dissociated in ABV rats. "A" wave was not followed by "V" wave. (C) Mean PP interval of normal and AV block rats. There was no significant difference in PP interval between groups. (D) Mean RR interval of normal and AV block rats. AV block rats had significantly longer RR interval than normal rats (**$p<0.01$, n=5). P=P wave; R=R wave.

FIGS. 7(c and d) Under 10 mV stimulation, action potentials detected by ECG in Gelatin (c) and AMBA-gelatin (d) group. FIGS. 7(f and g) Signal captured by MEA showed the conduction in Gelatin (f) and AMBA-gelatin (g) group under 300 mV stimulation. FIGS. 7(h and i) Atrial myocardium attached on AMBA-gelatin showing significant higher action potential amplitude (h) and conductive velocity (i) compared with atrial myocardium attached on Gelatin when under a range of voltage stimulation (n=6/group, *$P<0.05$).

FIGS. 8(d and e) Representative optical mapping results under 0.5 v normal electrode pacing. Electrode was inserted near heart apex (d), and activation maps (e) showed stimulation did not pace the heart but induced a local depolarization, activation orientation is identified by black arrows. FIGS. 8(g and h) Representative optical mapping results under 0.5 v gelatin-electrode pacing. Electrode was inserted in the gelatin injection area near heart apex (g), and activation maps (h) showed stimulation did not pace the heart and gelatin injection area showed high noise, activation orientation was identified by black arrows. FIGS. 8(j and k) Representative optical mapping results under 0.5 v AMBA-electrode pacing. Electrode was inserted in the AMBA-gelatin injection area near heart apex (j), and activation maps (k) showed stimulation paced the heart successfully and the pacemaker point (area identified by tail of arrow) changed to the AMBA-gelatin injection area when given stimulation. Activation orientation is identified by black arrows.

FIG. 9(a-c) Representative ECG traces of normal electrode (a) gelatin-electrode (b) and AMBA-gelatin-electrode (c) with 5 v pacing. Duration of Q-T wave is identified with vertical bars and stimulation is identified with black arrows.

FIG. 10(c-e) Representative ECG traces under normal electrode (c) gelatin-electrode (d) and AMBA-gelatin-electrode (e) at 0.5 v pacing. Stimulation and cardiac rhythm were mutually independent in normal electrode and gelatin-electrode pacing while AMBA-gelatin-electrode pacing successfully induced whole heart depolarization and the heart was under pacing rhythm. Adenosine was used to induce atrioventricular block to slow heart rate and details of ECG trace are shown in the box. FIG. 10(f-h) Representative ECG traces of normal electrode (f) gelatin-electrode (g) and AMBA-gelatin-electrode (h) at 5 v pacing. Duration of Q-T wave is identified with vertical bars and stimulation with black arrows.

FIG. 13 shows AMBA-gelatin enhanced both regional and global field potential amplitude in fibrotic scar tissue. FIG. 13(A) Left anterior descending coronary artery (LAD) ligation was performed to induce myocardial infarction (MI) in rats. Gelatin or AMBA-gelatin were injected into the ligated area one week later. Regional field potential amplitude on the fibrotic scar tissue formed at 4 weeks post MI were measured by multielectrode array (MEA 36 electrode). FIG. 13(B) Representative electrograms recorded from the 36 terminals. FIG. 13(C) AMBA-gelatin injection into the scar area enhanced regional fibrotic scar tissue field potential amplitude evaluated by MEA. FIG. 13(D) Global fibrotic scar tissue field potential amplitude were evaluated by 8-lead catheters. FIG. 13(E) Representative electrograms recorded at the remote, border and scar area through the 8-lead catheters. FIG. 13(F) The ratio of scar/remote field potential amplitude was significantly higher in the AMBA-gelatin injected rats compared to the Gelatin-injected rats.

FIG. 14 shows AMBA-gelatin injection reduced spontaneous and induced arrhythmia and improved conduction velocity in the infarcted rat heart. FIG. 14(A) Left anterior descending coronary artery (LAD) ligation was performed to induce myocardial infarction (MI) in rats. Gelatin or AMBA-gelatin were injected into the ligated area one week later. Spontaneous premature ventricular contractions (PVCs, arrows) at 4 weeks post MI were measured by telemetry. FIG. 14(B) The AMBA-gelatin group had lower rate of spontaneous PVCs per hour compared to the Gelatin group. FIG. 14(C) Induced ventricular tachycardia (VT) and PVCs were evaluated by program electrical stimulation (PES). FIG. 14(D) The AMBA-gelatin group had lower rate of induced PVCs per hour compared to the Gelatin group. (E, F, G) Electrical signal conduction kinetics of the ex vivo Langendorff-perfused rat hearts were measured by perfusing rat hearts with the voltage-sensitive dye di-4-ANEPPS 4 weeks after MI. Optical mapping of electrical impulse propagation (arrows) through the left ventricle (LV) of the heart was performed. The start point is marked with a star. FIG. 14(H) Conduction velocity was significantly decreased in the infarcted hearts compared with that of the non-infarcted normal hearts. However, AMBA-gelatin treated hearts exhibited significantly greater conduction velocities than Gelatin-injected hearts.

DETAILED DESCRIPTION

Figure 1:
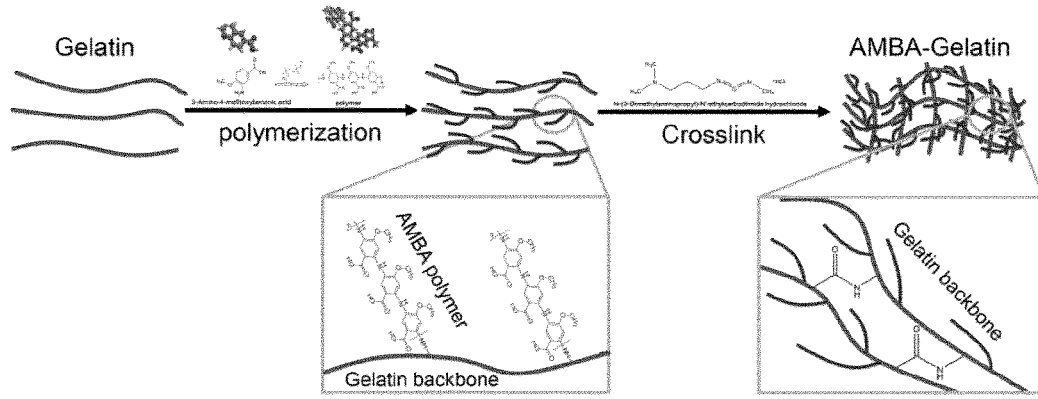
FIG. 1 shows schematic diagram showing the polymerization of Gelatin and 3-amino-4-methoxybenzoic acid (3-4-AMBA) monomers with ammonium persulfate (APS) followed by a crosslinking reaction with N-(3-Dimethylaminopropyl)-N'-ethylcarbodiimide hydrochloride (EDC) to form 3-4-AMBA-gelatin hydrogel.

Patients with congenital or acquired conduction blocks lack the normal propagation of electrical impulses and synchronous ventricular contraction. Clinical studies demonstrated that pacemakers prevented progress of heart failure. However, there are limitations with the use of pacemakers and myocardial fibrosis after myocardial infarction (MI) or lack of cardiac tissue at the site of congenital defects displays a significant non-synchronous disorder. A biocompatible conductive biomaterial that restores physiological propagation may synchronize contraction, restore ventricular function, and permit patients to return to a more active lifestyle.

The present disclosure relates to a biocompatible, electrically conductive biomaterial (a "biocompatible biomaterial") capable of carrying the electrical potential of a cardiac impulse, as well as treatments using the electrically conductive biomaterial. In particular, the present disclosure relates to the treatment of heart conditions such as MI by introducing a biocompatible, electrically conductive biomaterial to the heart. In some embodiments, the present disclosure permits propagation of electrical impulses both into and across biomaterials. The injection of a conductive biomaterial can be an efficacious technique to introduce biomaterial to the heart for the purpose of changing the conductive characteristics of the injured heart. In some embodiments, a conductive biomaterial creates or enhances electrical conduction, treating the electrical delays or blocks by acting as a bridge.

Definitions

As used herein, the term "aminomethoxybenzoic acid" or "AMBA" means a compound represented by the formula:

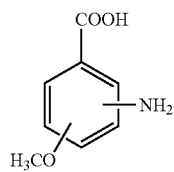

(I)

as well as derivatives and mixtures thereof as well as salts of any of the foregoing. Examples of AMBA include 3-amino-4-methoxybenzoic acid (3-4-AMBA), 4-amino-2-methoxybenzoic acid (4-2-AMBA), 2-amino-4-methoxybenzoic acid (2-4-AMBA), 4-amino-3-methoxybenzoic acid (4-3-AMBA), 5-amino-2-methoxybenzoic acid (5-2-AMBA), derivatives thereof and mixtures thereof. AMBA can be synthesized using methods that are known in the art, and can be purchased for example from chemical companies such as Sigma Aldrich (MO).

An "AMBA polymer" or "AMBA based polymer" as used herein means any polymer made using AMBA, optionally wherein the polymer is entirely made using AMBA.

As used herein, the term "biocompatible" refers to an article that does not cause toxic or injurious effects on a biological system.

As used herein, the term "biomaterial" refers to a polymer composition, hydrogel or article that is for augmenting or replacing partially or totally any tissue, organ or function of the body. The biomaterial can include an article in different physical forms, such as a hydrogel, membrane, sponge, optionally a sheet, 3D-patch or sponge or mesh for grafting. These forms include typical membranes, sheets, 3D-patches or sponges, or meshes for grafting, etc. used in surgery or tissue repair, for example after cardiac surgery. These articles can include natural products, synthetic products, or combinations thereof. The biomaterial of the present disclosure can be used exclusively to form one of these articles or can be used as a component of one of these articles.

The term "conjugated" as used herein in reference to a first compound and a second compound means that the first compound is coupled to the second compound, optionally electrostatically and/or via a covalent bond.

The term "amino" as used herein means a —$NH_2$ group.

As used herein, the term "hydrogel" refers to a polymeric material, typically a network or matrix of polymer chains, capable of swelling in water or becoming swollen with water. A hydrogel can also be understood to be a material that retains water in an equilibrium state. The network or matrix may or may not be crosslinked.

As used herein, a "conductive polymer" means a polymer that is inherently or intrinsically capable of electrical conductivity.

As used herein, a "biocompatible component" means or includes natural products, synthetic products or combinations thereof. In one embodiment, the biocompatible component can include a natural product, such as a linear or branched polysaccharide, protein or polypeptide. These natural products include for example chitosan, gelatin, collagen, fibronectin, elastin, alginate, and derivatives and combinations thereof. In another embodiment, the biocompatible component can include a synthetic product, such as a biodegradable synthetic polymer.

As used herein, the term "gelatin" refers to a polypeptide product derivative of collagen typically composed of a heterogeneous mixture of polypeptides, and includes Type A and Type B gelatin. Gelatin can for example, be obtained by acid treating collagen or heating collagen at a suitable temperature. Gelatin can be derived from mammalian collagen such as bovine, porcine or ovine collagen, as well as from marine collagen or avian collagen. Gelatin can be used, for example, as a sponge such as GELFOAM®.

As used herein, the term "conduction abnormality" means a disorder caused by improper electrical impulses through the heart. Conduction abnormalities include for example bundle branch block, for example right bundle branch block and left bundle branch block; heart block, for example first-degree heart block, second-degree heart block, third-degree or complete heart block, left anterior hemiblock, left posterior hemiblock, bifascicular black, trifascicular block; and long Q-T Syndrome. Conduction abnormality may be for example caused by abnormal function of heart cells, including heart conductive cells, cardiomyocytes or fibroblasts, by death of cardiomyocytes or conductive cells, or by heart abnormality induced by accumulation of fibrotic tissue in heart.

As used herein, the term "genipin" is meant to include a compound recognized as genipin as a chemical compound or an equivalent of genipin as a chemical compound by a person of ordinary skill in the art. The term "genipin" is intended to cover derivatives, analog, stereoisomers and mixtures thereof. The genipin compound can be derived from natural sources or synthetically made.

As used here, an "implantable device comprising an electrode" means an implantable electronic device. The implantable device comprising an electrode can include, for example, pacemakers, implantable cardioverter defribrillators (ICDs), and cardiac resynchronizing therapy (CRT) devices.

The term "treating" or "treatment" as used herein and as is well understood in the art, means an approach for obtaining beneficial or desired results, including clinical results. Beneficial or desired clinical results can include, but are not limited to alleviation or amelioration of one or more symptoms or conditions, diminishment of extent of disease, stabilized (i.e. not worsening) state of disease, preventing spread of disease, delay or slowing of disease progression, amelioration or palliation of the disease state, diminishment of the reoccurrence of disease, and remission (whether partial or total), whether detectable or undetectable. For example, a subject with a heart condition can be treated to prevent progression, of the heart condition, or alternatively, a subject with a heart condition can be treated to improve the heart condition by, for example, improving cardiac pacing, cardiac conductivity and/or cardiac conductivity propagation. "Treating" and "treatment" can also mean prolonging survival as compared to expected survival if not receiving treatment. "Treating" and "treatment" as used herein also include prophylactic treatment.

As used in this specification and the appended claims, the singular forms "a", "an" and "the" include plural references unless the content clearly dictates otherwise. Thus for example, a composition containing "a compound" includes a mixture of two or more compounds. It should also be noted that the term "or" is generally employed in its sense including "and/or" unless the content clearly dictates otherwise.

As used in this application and claim(s), the word "consisting" and its derivatives, are intended to be close ended terms that specify the presence of stated features, elements, components, groups, integers, and/or steps, and also exclude the presence of other unstated features, elements, components, groups, integers and/or steps.

The terms "about", "substantially" and "approximately" as used herein mean a reasonable amount of deviation of the modified term such that the end result is not significantly changed. These terms of degree should be construed as including a deviation of at least ±5% or at least ±10% of the modified term if this deviation would not negate the meaning of the word it modifies.

The definitions and embodiments described in particular sections are intended to be applicable to other embodiments herein described for which they are suitable as would be understood by a person skilled in the art. For example, in the following passages, different aspects are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Biocompatible Conductive Biomaterials and Methods of Using

A first aspect provided herein relates to a biocompatible conductive biomaterial comprising a conductive polymer and a biocompatible component.

A second aspect provided herein is a method of making a biocompatible conductive biomaterial the method comprising conjugating a conductive polymer and a biocompatible component.

The conductive polymer can include benzoic acid based polymers, and mixtures or copolymers thereof. In particular, the conductive polymer can be or comprise an aminomethoxybenzoic acid (AMBA) based polymer.

In some embodiments, the aminomethoxybenzoic acid (AMBA) is 3-amino-4-methoxybenzoic acid (3-4-AMBA). In some embodiments, the aminomethoxybenzoic acid is 4-amino-2-methoxybenzoic acid (4-2-AMBA). In some embodiments, the am inomethoxybenzoic acid is 2-amino-4-methoxybenzoic acid (2-4-AMBA). In some embodiments, the aminomethoxybenzoic acid is 4-amino-3-methoxybenzoic acid (4-3-AMBA). In some embodiments, the am inomethoxybenzoic acid is 5-amino-2-methoxybenzoic acid (5-2-AMBA). AMBA can be synthesized through methodologies well known in the art from other substituted benzenes using, e.g., nucleophilic or electrophilic aromatic substitutions.

In some embodiments, the aminomethoxybenzoic acid includes:

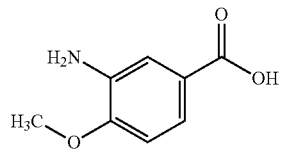

and salts thereof.

In some embodiments, the aminomethoxybenzoic acid includes:

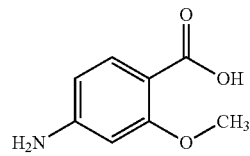

and salts thereof.

In some embodiments, the aminomethoxybenzoic acid includes:

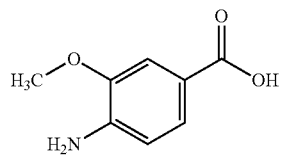

and salts thereof.

In some embodiments, the aminomethoxybenzoic acid includes:

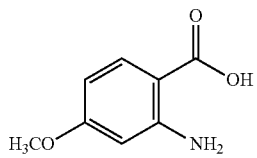 [SMILES: COc1ccc(C(=O)O)c(N)c1]

and salts thereof.

In some embodiments, the aminomethoxybenzoic acid includes:

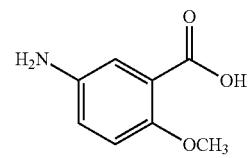

and salts thereof.

The conductive polymer can be linear or branched. In some embodiments, the molecular weight of the conductive polymer is greater than about 300 Daltons, or about 500

Daltons, or about 1,000 Daltons, or about 1,500 Daltons, or about 2,000 Daltons, or about 3,000 Daltons, or about 4,000 Daltons, or about 5,000 Daltons, or about 7,000 Daltons, or about 9,000 Daltons, or about 10,000 Daltons, or about 12,000 Daltons, or about 14,000 Daltons, or about 16,000 Daltons. In other embodiments, the molecular weight of the conductive polymer is less than about 200 Daltons, or about 500 Daltons, or about 1,000 Daltons, or about 1,500 Daltons, or about 2,000 Daltons, or about 3,000 Daltons, or about 4,000 Daltons, or about 5,000 Daltons, or about 7,000 Daltons, or about 9,000 Daltons, or about 10,000 Daltons, or about 12,000 Daltons, or about 14,000 Daltons, or about 16,000 Daltons, or about 18,500 Daltons. In still other embodiments, the molecular weight can be a range between any of these values (e.g., between about 200 Daltons and about 7,000 Daltons, or between about 50 Daltons and about 10,000 Daltons, etc.).

In an embodiment, the biocompatible component comprises a natural product, a synthetic product, and mixtures thereof.

In an embodiment, the natural product is selected from gelatin, chitosan, collagen, fibronectin, elastin, alginate, and derivatives and mixtures thereof.

In one embodiment, the biocompatible component comprises or is gelatin. Gelatin is a derivative of collagen, and is widely used in tissue engineering field for its biocompatibility and mechanical properties.

In another embodiment, the biocompatible component comprises a synthetic product, for example a biodegradable synthetic polymer.

The biocompatible component can have a molecular weight ranging from about 50,000 to about 150,000 Daltons optionally from about 50,000 Daltons to about 100,000 Daltons. In some embodiments, the molecular weight is greater than about 50,000 Daltons, or about 60,000 Daltons, or about 70,000 Daltons, or about 80,000 Daltons, or about 90,000 Daltons or about 100,000 Daltons or about 110,000 Daltons, or about 120,000 Daltons, or about 130,000 Daltons. In other embodiments, the molecular weight of the biocompatible component is less than about 60,000 Daltons, or about 70,000 Daltons, or about 80,000 Daltons, or about 90,000 Daltons, or about 100,000 Daltons, or about 110,000 Daltons, or about 120,000 Daltons or about 130,000 Daltons, or about 140,000 Daltons or about 150,000 Daltons.

The conductive polymer and the biocompatible component can be combined, for example by chemical conjugation, to form an electrically conductive biocompatible biomaterial. The molar ratio of the conductive polymer and biocompatible component in the biomaterial can range from 1000:1 to 1:1000, respectively. In some embodiments, the molar ratio of the conductive polymer and biocompatible component can be greater than about 1:3, or about 1:2, or about 1:1, or about 2:1, or about 3:1, or about 5:1, or about 10:1, or about 25:1, or about 50:1, or about 100:1, or about 150:1, or about 200:1, or about 250:1, or about 300:1 or about 350:1 or about 400:1, or about 500:1. In other embodiments, the molar ratio of the conductive polymer and biocompatible component can be less than about 1:2, or about 1:1, or about 2:1, or about 3:1, or about 5:1, or about 10:1, or about 25:1, or about 50:1, or about 100:1, or about 150:1, or about 200:1, or about 250:1, or about 300:1 or about 350:1 or about 400:1, or about 500:1, or about 1000:1. In still other embodiments, the molar ratio of the conductive polymer and biocompatible component can be a range between any of these values (e.g., between 1:1 to 1:350, or between 1:3 to 1:150, or between 3:1 and 300:1, etc.). In one embodiment, the ratio is 2:1 to 1000:1. In one embodiment, the molar ratio is about 30:1 to about 60:1.

In some embodiments, the molecular weight of the biocompatible conductive biomaterial can range from about 50,000 to about 1,000,000 Daltons. In some embodiments, the molecular weight of the biomaterial is greater than about 50,000 Daltons, or about 60,000 Daltons or about 75,000 Daltons, or about 100,000 Daltons, or about 150,000 Daltons, or about 200,000 Daltons, or about 300,000 Daltons, or about 400,000 Daltons, or about 500,000 Daltons, or about 600,000 Daltons, or about 700,000 Daltons, or about 800,000 Daltons. In other embodiments, the molecular weight of the biocompatible conductive biomaterial is less than about or about 60,000 Daltons, or about 75,000 Daltons, or about 100,000 Daltons, or about 150,000 Daltons, or about 200,000 Daltons, or about 300,000 Daltons, or about 400,000 Daltons, or about 500,000 Daltons, or about 600,000 Daltons, or about 700,000 Daltons, or about 800,000 Daltons, or about 1,000,000 Daltons. In still other embodiments, the molecular weight of the biocompatible conductive biomaterial can be a range between any of these values (e.g., between about 50,000 Daltons and about 800,000 Daltons, or between about 150,000 Daltons and about 300,000 Daltons, etc.).

In one embodiment, the conductivity of the biomaterial is greater than, at least or equal to about $10^{-6}$ S/cm or greater than, at least or equal to about $10^{-5}$ S/cm. In some embodiments, the conductivity of the biomaterial is greater than, at least or equal to about $10^{-5}$ S/cm, or about $10^{-4}$ S/cm, or about $10^{-3}$ S/cm or about $10^{-2}$ S/cm. For example, the range may be from about $10^{-6}$ S/cm to about $10^{-2}$ S/cm, or to about $10^{-1}$ S/cm. As shown in FIG. 7(h) a biocompatible conductive biomaterial prepared according to a method as described herein increased the amplitude of action potentials when tissue was stimulated between 0 and 100 mV in the presence of AMBA-gelatin compared to gelatin alone. In particular embodiments, the materials are able to carry the electrical potential of a cardiac impulse of about 10 to about 110 mV, or about 20 to about 100 mV, or about 50 to about 100 mV, or about 75 to about 100 mV, or any combination of these values (e.g., about 50 to about 100 mV, etc.)

In an embodiment, the biocompatible conductive biomaterial has a conductivity of at least or greater than about 2-fold, at least or greater than about 3-fold, at least or greater than about 4-fold, at least or greater than about 5-fold, at least or greater than about 6-fold, at least or greater than about 7-fold, at least or greater than about 8-fold, at least or greater than about 9-fold, at least or greater than about 10-fold, at least or greater than about 11-fold, at least or greater than about 12-fold, at least or greater than about 13-fold, at least or greater than about 14-fold, at least or greater than about 15-fold or at least or greater than about or up to 20-fold or 25 fold greater than a control biomaterial that does not comprise the conductive polymer.

The biomaterial can comprise other components. For example, an AMBA-gelatin sponge can comprise gelatin and other components such as other polypeptides.

In an embodiment, the biomaterial is a liquid solution, a hydrogel, a membrane, a 3D-patch or sponge, a sheet, or a mesh for grafting. For example as shown in the Examples, AMBA can be conjugated to gelatin using APS, the conjugated material being in liquid form. The solution is then cross-linked using for example EDC to cross-link the AMBA-gelatin solution into hydrogel. When using a gelatin sponge such as Gelfoam or other scaffold such as a mesh etc, APS can be used to conjugate AMBA to the gelatin sponge (or scaffold) and a crosslinking agent such as EDC is not necessary.

AMBA-gelatin formed as a sheet or 3D-patch or sponge (3D-patch and sponge are used interchangeably) can be used, for example, as a protective cover or to provide structural support to a tissue defect. AMBA-gelatin may be also formed as a mesh for grafting, for example, in repairing a tissue defect.

Methods for making the for making a liquid solution or a hydrogel comprising AMBA-gelatin, are described in the Examples. For example the method can comprise combining AMBA (one or more different AMBAs) and gelatin, polymerizing the AMBA and gelatin to produce conjugated AMBA-gelatin (e.g. liquid solution), and optionally cross-linking the AMBA-gelatin or cooling the liquid solution to form the hydrogel.

The AMBA can be polymerized conjugated to gelatin (optionally gelatin per se or a scaffold comprising gelatin) using APS. Where gelatin or other biocompatible polymer is used without compression or scaffold, the AMBA-gelatin can be cross-linked using for example EDC.

The biocompatible conductive biomaterial, for example, when a solution, can be crosslinked using a crosslinking agent to assist in hydrogel formation. For example, as shown in the Examples, the AMBA-Gelatin polymers can be cross-linked to form the cross-linked hydrogel. The crosslinking agent can be a known crosslinking agent and contain electrophilic groups, nucleophilic groups, or both. The cross-linking agent can be a natural product or a synthetic product. Examples of multi-functional crosslinking agents which may be used include, for example, EDC, N-Hydroxysuccin-imide, gluteraldehyde, methylene-bis-acrylamide, diethylene glycol diacrylate, ethylene glycol diacrylate, triethylene glycol-bis-methacrylate, ethylene glycol-bis-methacrylate, ethylene glycol-dimethacrylate, bisacrylamide, triethyleneglycol-bis-acrylate, 3,3'-ethylidene-bis(N-vinyl-2-pyr-rolidone), trimethylolpropate trimethacrylate, glycerol trimethacrylate, polyethylene glycol dimethacrylate, other polyacrylate and polymethacrylate esters, and mixtures thereof. In one embodiment, the crosslinking agent is EDC. In one embodiment, the crosslinking agent is genipin or tannic acid.

The ratio of crosslinking agent to biocompatible conductive biomaterial can be within the range of about 2:100,000 to about 5:1,000 by volume. The crosslinking agent can be added to the biomaterial just prior to introduction to the target location (for example, the heart) (e.g., 1-10 minutes prior to introduction). In some embodiments, it takes 1-10 minutes for the biomaterial to gel. During the gelling time, the biomaterial can be introduced to the target location (for example, the heart).

In an embodiment, the hydrogel comprises an aminomethoxybenzoic acid (AMBA) polymer and gelatin. For example, as detailed in the Examples, the AMBA polymer is conjugated to one or more amino groups of gelatin.

In an embodiment, the water content of the hydrogel is about 75 wt. % to about 95 wt. %. For example, the water content is about 80 wt. %. For example, the water content is about 82 wt. %. For example, the water content is about 85 wt. %. For example, the water content is about 90 wt. %.

In an embodiment, the biocompatible conductive biomaterial is synthesized according to a method described in Examples 1 and 4 detailed below.

Another aspect provided herein relates to a device utilizing one of the biocompatible biomaterials described herein.

The device can be an implantable device comprising an electrode.

In one embodiment, the implantable device comprises at least one electrode coated at least partially by a biocompatible conductive biomaterial comprising at least one of the conductive polymers described herein. For example, the biocompatible conductive biomaterial can be injected into cardiac tissue in need of improvement in conduction (such as, for example, the atrial ventricular node) and the electrode inserted into the biomaterial either during or after gelling, such that the electrode is then coated. As an another example, the biocompatible conductive biomaterial can be formed into a cast shape around the end of the electrode, the shape corresponding to an injection site of predetermined size within the cardiac tissue.

In an embodiment, the implantable device is a cardiac pacemaker.

For example, the cardiac pacemaker can be a single chamber pacemaker, a dual chamber pacemaker or a biventricular pacemaker.

In another embodiment, the device is an implantable cardioverter defibrillator (ICD) wherein at least one electrode is coated at least partially by a biocompatible conductive biomaterial comprising at least one of the conductive polymers described herein.

In one embodiment, the lead of the pacemaker or ICD is coated at least partially by the biocompatible biomaterial.

Dual function devices comprising pacemaker and ICD capability are also contemplated.

Yet another aspect relates to a kit comprising a device with an electrode such as a pacemaker and a biocompatible conductive biomaterial comprising a conductive polymer and a biocompatible component, the conductive polymer comprising for example an aminomethoxybenzoic acid (AMBA) polymer. In one embodiment, the kit comprises instructions for implanting the device and introducing the biocompatible conductive biomaterial such that it surrounds the electrode when implanted.

The biocompatible conductive biomaterial can also be used for cardiac repair of a cardiac defect or as a platform for growing cardiomyocytes to generate cardiac tissue. The conductivity for example of 3D patches or sponges can synchronize the cardiomyocytes in the patch as indicated in Example 6. The biocompatible conductive biomaterial (e.g. as a patch) alone or with cardiomyocytes can be used to repair congenital cardiac defects as well as for example surgical repair of dilated heart of patients with congestive heart failure.

Accordingly in another embodiment, is provided a composition comprising the biocompatible conductive biomaterial, optionally as a hydrogel or sheet, 3D-patch or sponge, or mesh and one or more of culture media and cardiomyocytes.

In another embodiment, the present disclosure relates to a method of ameliorating or treating a heart condition, the method comprising introducing a biocompatible conductive biomaterial to the heart in a subject in need thereof, wherein the biomaterial includes a conductive polymer and a biocompatible component described herein.

For example, the heart condition can include myocardial infarction, ischemic myocardium, myocardial fibrosis, heart failure, atrioventricular block, arrhythmia, bradycardia and a conduction abnormality for example resulting from cardiac surgery.

The AMBA-gelatin optionally in hydrogel form, can also be used to reestablish conduction created by cardiac surgery. For example in cardiac valve replacement, the damaged valve is removed surgically. The surgery may damage surrounding cardiac tissue and can result in conduction block (a side effect of valve treatment). It has been reported that transcatheter aortic valve replacement (TAVR), which is a well-accepted option for treating patients with aortic disease, can result in TAVR-related conduction disturbances, mainly new-onset left bundle-branch block and advanced atrioventricular block requiring permanent pacemaker implantation.

Accordingly, hydrogels and other forms of the biocompatible conductive biomaterial described herein can be injected to restore conduction in such situations.

In an embodiment, the biocompatible conductive biomaterial is introduced into or onto the affected area of the heart.

For example, the biocompatible conductive biomaterial can be introduced into or onto heart tissue in proximity to the interface with where a lead of a pacemaker or other device will attach. As shown herein, this reduces resistance of the tissue for lead stimulation.

In an embodiment, the biocompatible conductive biomaterial is introduced into or onto the affected area of the heart, for example into or onto fibrotic scar tissue. As shown in the Examples, this can reduce the occurrence of cardiac arrhythmia. In an embodiment, the biocompatible conductive biomaterial is for increasing cardiac conductivity.

In an embodiment, the amount of biocompatible conductive biomaterial introduced is sufficient to increase cardiac tissue conductivity by at least 2-fold, at least 3-fold, at least 4-fold, at least 5-fold, at least 6-fold, at least 7-fold, at least 8-fold, at least 9-fold, or at least 10-fold compared to an untreated control.

In an embodiment, the biocompatible conductive biomaterial is for synchronizing in sequence (atrial beat first followed by ventricular contraction) the atrioventricular heartbeat of the subject.

As demonstrated herein, the biocompatible conductive biomaterial can also be used to reduce the pacing threshold voltage of a cardiac pacemaker. Accordingly, the biocompatible compositions can be used to increase myocardium reactivity to heart pacing in a subject in need thereof.

In such embodiments, the biocompatible conductive biomaterial can be introduced proximal to one or more electrodes of the pacemaker in a subject comprising a pacemaker or in a subject receiving a pacemaker implant. The biocompatible conductive biomaterial may be introduced prior to or after the subject receives the pacemaker implant.

In one embodiment, the biocompatible conductive biomaterial is introduced into or onto the heart of the subject followed by pacing the heart with a pacemaker or implantation of a ICD or dual ICD pacemaker.

Also contemplated are methods using an implantable device such as a pacemaker or ICD wherein one or more electrodes of the pacemaker are at least partially coated with a biocompatible conductive biomaterial described herein.

In one embodiment, the biocompatible conductive biomaterial is for decreasing cardiac pacing threshold voltage.

In a further embodiment, the amount of biocompatible conductive biomaterial introduced is sufficient to decrease cardiac pacing threshold voltage by at least 2-fold, at least 3-fold, at least 4-fold, or at least 5-fold compared to an untreated control.

In an embodiment, the biocompatible conductive biomaterial is for increasing the amplitude of a cardiac action potential, increasing cardiac conductive velocity or decreasing QT interval duration.

In yet another embodiment, the amount of biocompatible conductive biomaterial introduced is sufficient to increase cardiac action potential amplitude induced by the pacemaker by at least about 10%, at least about 20%, at least about 30%, at least about 40% or at least about 50% compared to an untreated control.

In an embodiment, the amount of biocompatible conductive biomaterial introduced is sufficient to increase cardiac conductive velocity by at least about 10%, at least about 20%, at least about 30%, at least about 40% or at least about 50% compared to an untreated control.

In an embodiment, the amount of biocompatible conductive biomaterial introduced is sufficient to decrease QT interval duration and/or cardiac action potential duration by at least about 10%, at least about 20%, at least about 30%, at least about 40% or at least about 50% compared to an untreated control.

In another embodiment, the subject is a mammal, optionally a rat, a mouse or a human. In an embodiment, the subject is a human.

A further aspect provided herein is the use of a biocompatible conductive biomaterial described herein or a conductive hydrogel described herein to treat a heart condition and/or to increase myocardial reactivity to heart pacing in a subject in need thereof.

The biocompatible conductive biomaterial (e.g., hydrogel) can be introduced by known methods of treating biological tissue and organs with a hydrogel and similar materials. In an embodiment, the biomaterial is introduced by needle injection, optionally image guided needle injection, into or onto the affected area. In one embodiment, the biocompatible conductive biomaterial can be injected into or onto the heart, for example the atrial ventricular conductive node and surrounding area.

In one embodiment, the biocompatible conductive biomaterial is introduced (optionally needle injected) prior to solidification into or onto the affected area. The biomaterial subsequently solidifies (e.g. becomes gelled). In another embodiment, the biomaterial is introduced in a precast form, for example precast into fiber, sheet, 3D-patch or sponge, or mesh, and then implanted into the affected area.

The biocompatible conductive biomaterials can also be formed in sheet, or other articles such as a 3D-patch, which can be used on top of the injured tissue or to surround, for example, a device such as a pacemaker's electrode connection to the heart.

In one embodiment, the amount of the biocompatible conductive biomaterial (e.g., hydrogel) introduced to the tissue or organ can depend on a number of factors, such as the composition of the biomaterial, the location and the condition of the tissue or organ, the purpose for introducing the biomaterial (e.g. treating MI or reducing pacing threshold), the size of the tissue or organ and/or the size of the damaged or area to be treated. In one embodiment, the volume of biomaterial can range from about 1 μl to about 10 mL, or about 2 μl to about 5 mL, or about 5 μl to about 3 mL, or about 10 μl to about 2 mL, or about 50 μl to about 1 mL, or about 100 μl to about 500 μl, or any combination of these values (e.g., about 1 mL to about 2 mL, etc.)

As shown herein, the biocompatible conductive biomaterial is effective in hearts with fibrotic scar tissue. Accordingly, in some embodiments the subject has suffered a cardiac infarct and/or has scar tissue.

The disclosures of all cited references including publications, patents, and patent applications are expressly incorporated herein by reference in their entirety.

When an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

The present invention is further defined in the following Examples. It should be understood that these Examples, while indicating preferred embodiments of the invention, are given by way of illustration only.

EXAMPLES

Example 1—Synthesis of AMBA-Gelatin Hydrogel and Gelatin Sponge

Figure 2A:
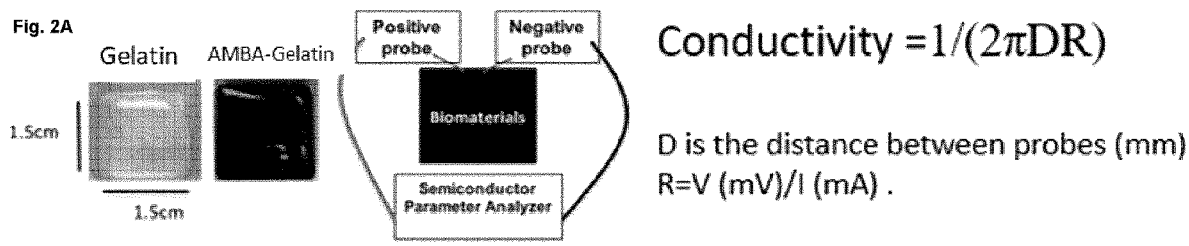
FIG. 2 shows conductivity measurement of Gelatin and AMBA-gelatin or AMBA-gelatin sponge. AMBA-gelatin or Gelatin was placed into a 1.5 cm*1.5 cm dish to test the conductivity. (A). Schematic of the apparatus used to measure biomaterial resistance (R). The distance between each electrode is 1.5 cm. The conductivity (measured in S/cm) is calculated as $1/(2\pi DR)$, where D is the distance between probes (mm), R=V/I, I is the supplied current (mA) and V is the corresponding voltage (mV). (B). The AMBA-gelatin has about 5-fold higher conductivity compared with the Gelatin group (**$p<0.01$, n=72). (C) Gelatin sponge (Gelfoam®) (Gelfoam, left), AMBA mixed with Gelfoam® (AMBA+Gelfoam, centre) and AMBA conjugated to Gelfoam® after treatment with ammonium persulfate (APS) (MBA-Gelfoam, right). (D) AMBA conjugated to Gelfoam® after treatment with ammonium persulfate has higher conductivity compared to Gelfoam® or AMBA mixed with Gelfoam®.
Figure 2B:
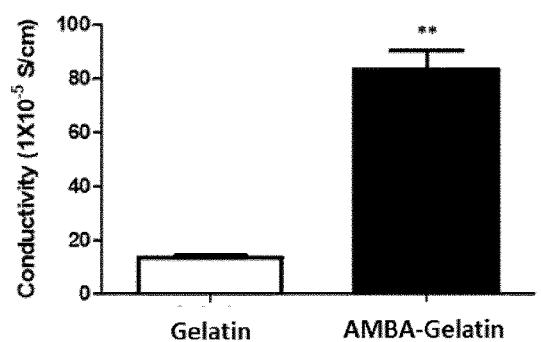
Figure 2C:
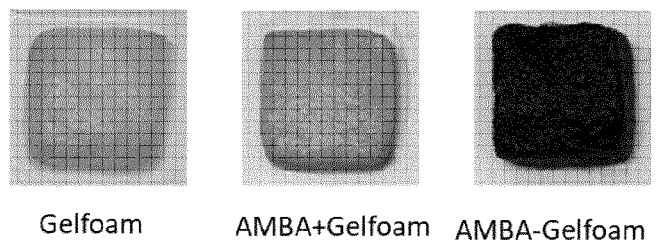
Figure 2D:
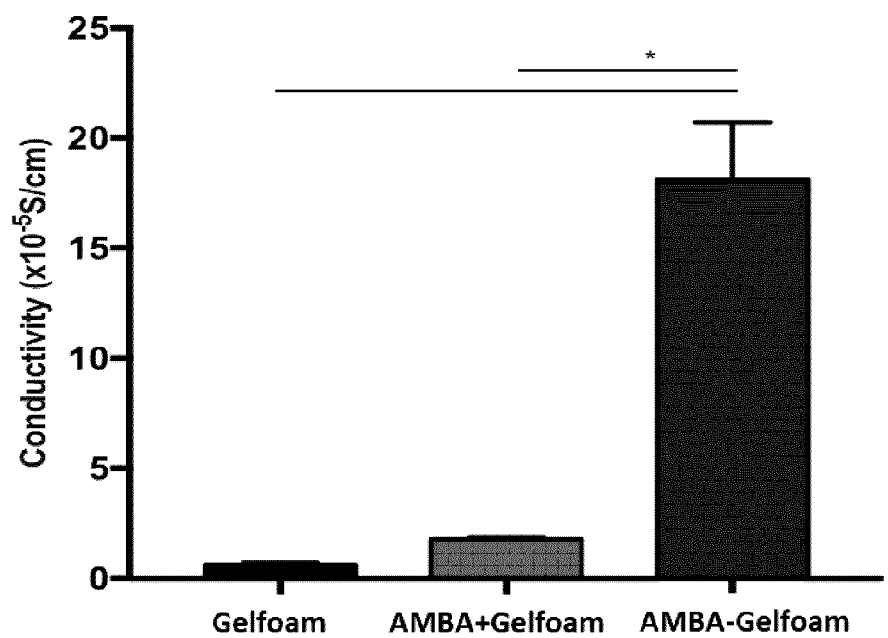

A conductive hydrogel that was able to be injected into cardiac tissue with some liquidity was generated and found to have appropriate conductivity that permits cardiac impulse propagation. Polymerized AMBA (poly-AMBA) is a conductive polymer (FIG. 1). However, poly-AMBA without additional processing is non-thermoplastic, mechanically rigid and brittle, and is not optimal for cardiac applications. AMBA was polymerized and conjugated to gelatin to generate an AMBA-gelatin conductive solution which was subsequently crosslinked to form AMBA-gelatin hydrogel (FIG. 1 and FIGS. 2A and B). AMBA was also polymerized and conjugated onto a gelatin sponge (Gelfoam®) to generate a conductive AMBA-gelatin sponge (AMBA-Gelfoam) (FIG. 2C).

The conductive biomaterial was generated by conjugating conductive poly 3-amino-4-methoxybenzoic acid (AMBA) onto gelatin. 2 g Gelatin powder (LOT NO. 895893A, Fisher Scientific, Canada) was dissolved in 10 ml deionized distilled water under mechanical stirring, then 0.2 g 3-amino-4-methoxybenzoic acid powder (B20669, Alfa Aesar, MA) was added in the solution. After the powder was totally dissolved, 0.546 g ammonium persulfate (APS) (AMMONIUM PERSULFATE, CAS #7727-54-0, Bio Basic Canada Inc.) was added to the solution to polymerize the AMBA and link the AMBA polymer to the amino groups of the gelatin to form the AMBA-gelatin solution. The polymerization reaction was maintained for 6 hours at 50 degree Celsius in a water bath. At last, the pH of the AMBA-gelatin solution was adjusted to about 7.0 with NaOH (Sigma-Aldrich). Before using, the AMBA-gelatin solution was cross-linked with 4 ul N-(3-Dimethylaminopropyl)-N'-ethylcarbodiimide hydrochloride (EDC, 22980, Thermo fisher, MA) and 2 ul N-Hydroxysuccinimide (NHS, 130672-5G, Sigma-Aldrich, MO) for 5 minutes to form AMBA-gelatin hydrogel.

Example 2—Conductivity Assessment

Figure 3:
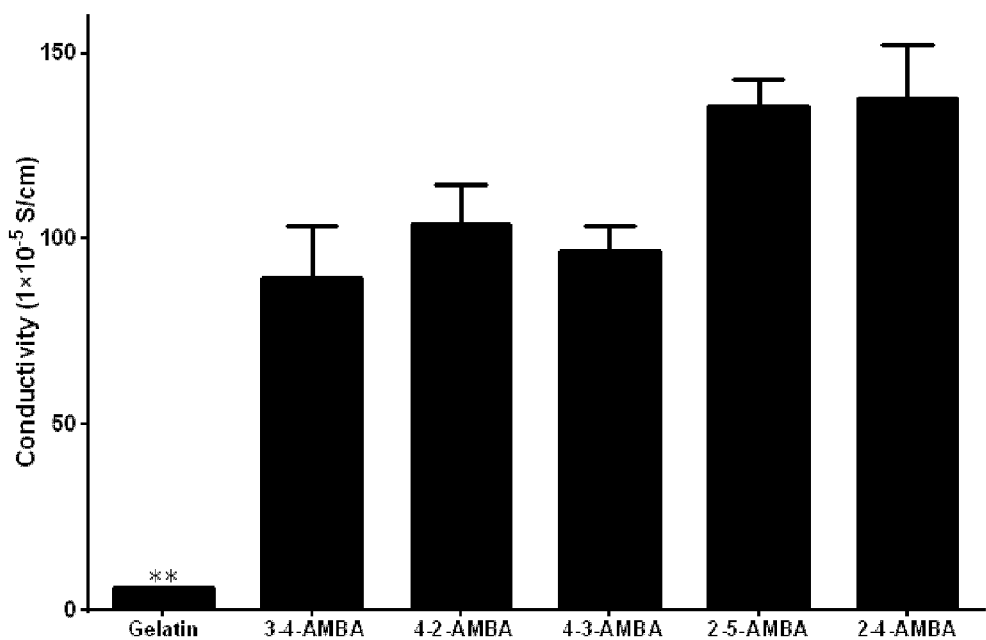
FIG. 3 shows conductivity measurement of polymeric 3-4-AMBA, 4-amino-2-methoxybenzoic acid (4-2-AMBA), 4-amino-3-methoxybenzoic acid (4-3-AMBA), 2-amino-5-methoxybenzoic acid (2-5-AMBA), and 2-amino-4-methoxybenzoic acid (2-4-AMBA) compared with Gelatin (**$p<0.01$).

A two-point probe resistivity apparatus (HF2IS, Zurich Instruments, Switzerland) was used to measure the biomaterial resistance at room temperature of the AMBA-gelatin hydrogel made according to Example 1. The probes were placed on Gelatin and AMBA-gelatin hydrogel film with an interval of 1.5 cm. The conductivity (measured in S/cm) is calculated as $1/(2\pi DR)$, where D is the distance between probes (mm), and R=V/I where I is the supplied current (mA) and V is the corresponding voltage (mV). The resistance of AMBA-gelatin gelled in a 1.5 cm*1.5 cm dish and the biomaterial resistance was measured (FIG. 2A). The AMBA-gelatin hydrogel had about 5-fold higher conductivity (reciprocal of resistance) compared to Gelatin (FIG. 2B, **$p<0.01$, n=72). Different AMBA-gelatin hydrogels were made using different AMBAs, namely 3-4-AMBA, 4-2-AMBA, 4-3-AMBA, 2-5-AMBA and 2-4-AMBA, and all were found to have conductivity superior to the Gelatin hydrogel (FIG. 3).

Example 3—AVB Model

An AVB rat model was created by injecting ethanol into AV node of the heart. Rats with AVB were used to investigate the ability of the electrical conduction bridge effect of AMBA-gelatin in vivo. The electrocardiogram (ECG) profile was used to investigate. The propagation of the electrical current across the damaged AV node of AMBA-gelatin hydrogel-injected or gelatin-injected animals.

All experimental protocols were approved by the Animal Resource Centre of the University Health Network and conformed to the *Guide for the Care and Use of Laboratory Animals* (NIH, 8$^{th}$ Edition, 2011). Female SD rats weighing 235-250 g underwent ethanol-induced AV block as previously reported [10]. Briefly, ECGs were displayed on a physiological recorder. A 30-gauge needle connected to a microliter syringe (Hamilton, Reno, Nev.) was used to inject the solutions into the myocardium. To facilitate the direction of the needle toward the nodal tissue, the needle had been prepared by making a 90° bend in the shaft 3 mm from the tip. Thus the needle could only be inserted into the myocardium up to a maximum of 3 mm from the epicardial surface. After midline sternotomy and pericardiotomy, the tip of the right atrial appendage was reflected laterally to provide access to the AV junction in this area. This maneuver exposed the landmark for the epicardial approach to the AV node, a fat pad consistently located between the aortic root and the medial wall of the right atrium. This fat pad marks a point on the adventitial aspect of the aortic root corresponding to the commissure between the right and noncoronary leaflets of the aortic valve. The tip of the needle penetrated the epicardial surface at a point 1 mm posterior and 1 mm lateral to the fat pad. Directed toward the apex of the heart (i.e., in the long axis of the heart), the needle was inserted up to its bend. The angled portion of the needle was maintained parallel to the ascending aorta at all times. When the insertion of the needle resulted in momentary, complete AV block [as determined by electromechanical dissociation of the heart and electrocardiogram (ECG)], 50 µl of 70% ethanol were injected. After ethanol injury, Gelatin or AMBA-gelatin was injected into the AV node. Surface ECGs were obtained prior to ethanol injury. All animals were sacrificed post injection for morphological analysis.

Rats were anaesthetized by isoflurane and conventional surface ECG was used to monitor and record heart rhythm. The ECG electrodes were connected to atrial and ventricular heart muscle separately to monitor atrial and ventricular heart waves.

Data were expressed as mean±standard deviation. Analyses were performed using GraphPad Prism software (v.6.0), with the critical α-level set at $p<0.05$. Comparisons among multiple groups were made using one-way analysis of variance (ANOVA). When F values were significant, differences between the groups were investigated using Tukey's multiple range post-hoc test.

It was determined that AMBA-gelatin has 5-fold higher conductivity compared with gelatin. The ECG results demonstrated that stable, complete AVB was generated in 48 of 55 rats (87%). After injection of biomaterials into AVB rats, surface ECG results showed that the atrial rate had no significant differences indicating that any treatment did not impact the sinus impulse above the AV node. However, the ventricular rate was significantly faster in AMBA-gelatin-injected animals compared with gelatin only injected animals (290±87 vs. 60±28, p<0.01) suggesting that injection of AMBA-gelatin restored atrioventricular conduction block, whereas gelatin-injected hearts continued to have delayed propagation patterns compared to normal controls.

Figure 5:
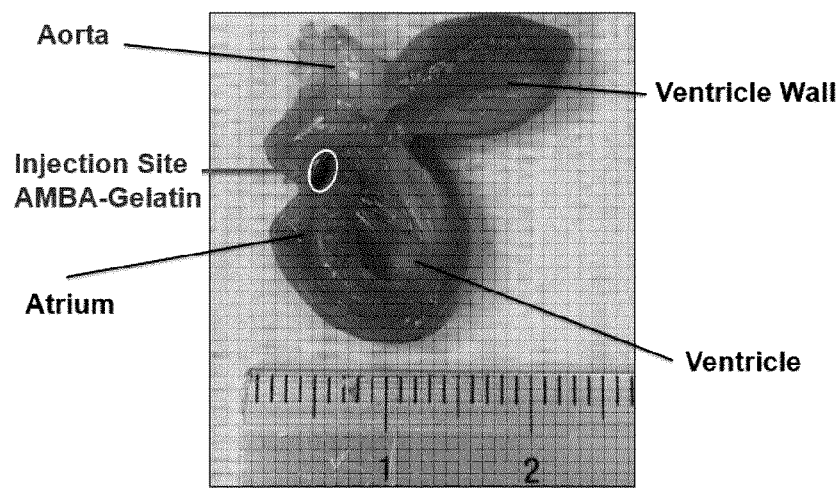
FIG. 5 shows the localization of 3-4-AMBA-gelatin injection site. AMBA-gelatin was injected into the AV node area (circle).
Figure 6A:
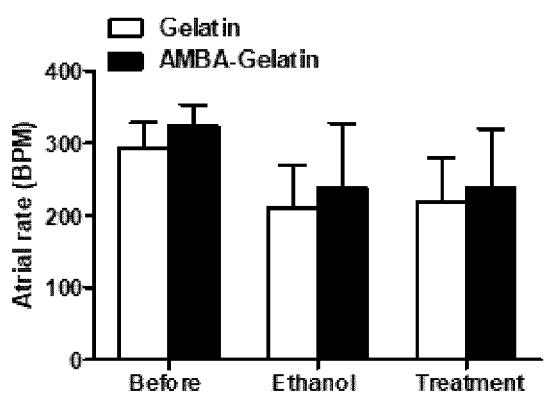
FIG. 6(A) shows the mean atrial rate (BPM) of Gelatin and 3-4-AMBA-gelatin-injected rats. There was no significant difference between groups at either before or after ethanol injection and gelatin treatment.
Figure 6B:
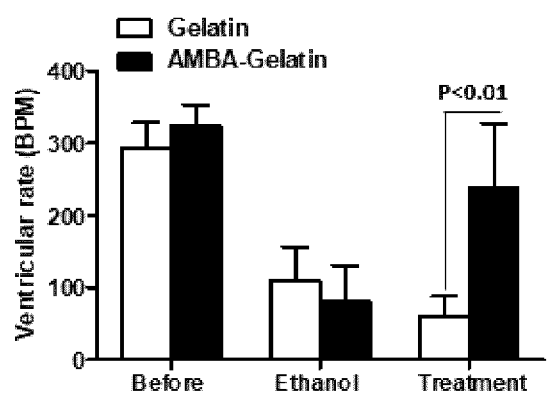
FIG. 6(B) shows the mean ventricular rate (BPM) of Gelatin- and AMBA-gelatin-injected rats. There was no significant difference between groups at before or after ethanol injection. However, AMBA-gelatin injection restored AVB heart beat to close normal and the heart beat is significantly higher than that of gelatin only injected rats ($P<0.01$, n=6).

Surface ECG was performed to record the atrial and ventricular depolarization and repolarization (FIGS. 4A and B). The ECG result showed that the P wave (P) to P interval of AVB rats was not prolonged compared with normal heart (FIG. 4C), but the R wave (R) to R interval was significantly prolonged compared with normal hearts (FIG. 4D, **p<0.01). Prolonged RR interval indicated that the ventricular depolarization is accepted from the level below the AV node and demonstrated that the conduction between the atria and ventricles of the heart is impaired because the pace does not reach the ventricles. The ability of AMBA-gelatin to function in the intact AVB heart in vivo was then evaluated. FIG. 5 demonstrated that AMBA-gelatin was successfully injected into the AV node area. Surface ECG results showed the atrium rate had no significant differences after ethanol-gelatin- or AMBA-gelatin-injection which indicated that any treatment did not impact the sinus impulse above the AV node level (FIG. 6A), but the ventricle rate was significantly faster after AMBA-gelatin-injection compared with Gelatin only injection (FIG. 6B, p<0.01). These results showed that the AMBA-gelatin restored the heart conduction propagation, whereas gelatin-injected hearts continued to have delayed propagation.

Thus AMBA-gelatin hydrogel may be useful in re-bridging AVB in the heart and restoring cardiac rhythm. The data showed that AMBA-gelatin injection restored AVB heart beat to close normal and the heart beat is significantly faster than that of gelatin only injected rats. These results also suggested that AMBA-gelatin not only has the advantage of gelatin but also could enable the impulse to propagate across this hydrogel. AMBA-gelatin, has elastic and hemostatic properties, and may be a conductive biomaterial for use in a wide variety of tissue engineering applications.

Example 4—Conductive AMBA-Gelatin Hydrogel Reduces Pacing Threshold Voltage of Cardiac Pacemaker Gelatin is a biocompatible natural protein and has good mechanical properties [19]. It forms part of the a composition of myocardial extracellular matrix but, it is not conductive. 3-amino-4-methoxybenzoic acid (3-4-AMBA), was conjugated to the side chains of gelatin to generate a conductive biomaterial AMBA-gelatin and its effect on cardiac pacing was investigated by injecting it into the myocardium electrode-tissue interface.
Methods:
AMBA-Gelatin Hydrogel Synthesis
AMBA-Gelatin Hydrogel was Synthesized as Described in Example 1. Assays of the Electrical Properties of AMBA-Gelatin Hydrogel A two-point probe resistivity apparatus (HF2IS, Zurich Instruments, Switzerland) was used to measure biomaterial resistance at room temperature. The probes were placed on Gelatin and AMBA-gelatin hydrogel film at an interval of 1.5 cm. The conductivity (measured in S/cm) was calculated as $1/(2\pi DR)$, where D is the distance between probes (mm), R=V/I; I is the supplied current (mA) and V is the corresponding voltage (mV).
Measurement of Electrode-Tissue Interface Conduction In Vitro Conduction of electrode-tissue interface was measured in vitro. Healthy rat heart atrial myocardium was isolated from the left atrium and linked to the stimulation electrodes via Gelatin or AMBA-gelatin on two sides respectively. The cathode was 5 mm away from the anode. A 3-lead Electrocardiograph (ECG) recorder (Power Lab, AD Instruments, CO) was used to detect myocardial action potentials and a multielectrode array (MEA, Multichannel Systems Reutlingen, Germany) was used to detect conductive velocity. Stimulation was from 1 mv to 100 mv for ECG recording and 100 mv to 1000 mv for MEA recording were provided with a stimulator (STG 4002, Multichannel Systems Reutlingen, Germany) and all stimulations were at 4 Hz with 4 ms duration. MEA data was analyzed with Cardio2D+ (Multichannel Systems Reutlingen, Germany).
Pacing Threshold Voltage Measurement in Langendorff Isolated Rat Heart Model All experimental protocols were approved by the Animal Resource Centre of the University Health Network and conformed to the Guide for the Care and Use of Laboratory Animals (NIH, 8th Edition, 2011). Female SD rats weighing 235-250 g were used in this study. To measure the threshold voltage the hearts were rapidly explanted and cannulated using a blunted 16 G needle via the aortic root on ice. Then the heart was retrograde-perfused with Krebs-Henseleit (K-H) solution (117 mM NaCl, 24 mM $NaHCO_3$, 11.5 mM dextrose, 3.3 mM KCl, 1.25 mM $CaCl_2$, 1.2 mM $MgSO_4$, 1.2 mM $KH_2PO_4$ equilibrated with 5% $CO_2$/95% $O_2$ gas) at 37° C. at 10 mL/min. To prevent motion noise, excitation-contraction coupling was blocked with 2, 3-butane dione monoxime (1 mg/ml, B-0753, Sigma-Aldrich, MO). The ECG was used to detect cardiac electrical activity and a stimulator (SD9, Grass, Canada) was used to stimulate the heart. Under K-H buffer perfusion, about 20 ul AMBA-gelatin hydrogel was injected into the myocardium near the ventricular apex. Then the cathode was inserted in the AMBA-gelatin area and anode electrode was inserted in the Krebs-Henseleit solution about 1.5 cm away from the cathode electrode. Stimulation was started from 0.5V and increased in increments of 0.1V until ventricular capture was achieved. The lowest value for a 100% pacing rhythm was recorded as pacing threshold voltage. In each group, 5.0V stimulation was performed and the ECG monitored for electrophysiological analysis. Normal electrode pacing without an injection and pacing stimulation in an area of gelatin injection pacing served as controls. All stimulations were 6 Hz with 4 ms duration.
Whole-Heart Optical Mapping A Langendorff perfusion procedure was performed as described above. Five minutes after cardiac recovery with spontaneous beating, the heart was perfused with the voltage-sensitive dye 4-(2-(6-(dibutylamino)-2-naphthalenyl) ethenyl)-1-(3-sulfopropyl)-pyridinium (di-4 ANEPPS; D1199, Invitrogen, CA) dissolved in Krebs Henseleit solution (25 μM) at a rate of 5 mL/min for 6 min. After administration of the dye, AMBA-gelatin hydrogel was injected and electrodes were inserted with the same method described above. 0.5V and 5.0V stimulation was adopted for the stimulator and the optical mapping data was recorded with the camera (Evolve 128, Photometrics, AZ). Custom made software based on Matlab (MathWorks, MA) was used for data analysis of the optical mapping signals [20]. Normal electrode pacing and gelatin injection pacing served as controls. All stimulations were 6 Hz with 4 ms duration.

Rat Atrioventricular Block Model

Adenosine (AD; 519 987, Boehringer Mannheim, German) was used to induce rat atrioventricular block (AV block). After median sternotomy, 150 ul AD (10 mg/ml) was rapidly injected via inferior vena cava to induce atrioventricular block and the time of the block was recorded. Then AD dose was adjusted to maintain the AV block duration at 120 seconds.

Pacing Threshold Voltage Measurement In Vivo

Rats were anaesthetized by isoflurane and conventional surface ECG was used to monitor and record heart rhythm. Median sternotomy was performed and after adequate heart exposure, 20 ul AMBA-gelatin hydrogel was injected into the right ventricle wall near heart apex. Then a cathode was inserted in the AMBA-gelatin area and an anode electrode was inserted subcutaneously on the left side of the sternum. Stimulation procedures were the same as previously described for the Langendorff isolated rat heart model and pacing threshold voltage values were recorded. ECGs under 5.0 v stimulation in each group were also recorded for electrophysiological analysis. Normal electrode pacing and gelatin injection pacing served as controls. All stimulations were 6 Hz with 4 ms duration.

Statistical Methods

Statistical Package for Social Sciences, version 22.0 (SPSS, Chicago, Ill.) was used for data analysis. Student's t test and one way ANOVA followed with HSD post hoc tests were adopted for two and groups respectively when variances were equal. Welch's t-test and Welch analysis of variance followed by Tamhane T2 post hoc testing were adopted for two and groups respectively when variances were not equal. Data were presented as mean±SD. $P<0.05$ was considered statistically significant.

Results

AMBA-Gelatin Hydrogel Synthesis and Characteristics

As shown in FIG. 1, AMBA was polymerized and conjugated to gelatin to generate a conductive AMBA-gelatin solution. Ammonium persulfate (APS) was used to catalyze the reaction. Before using, the AMBA-gelatin solution was cross-linked with 4 ul N-(3-Dimethylaminopropyl)-N'-ethylcarbodiimide hydrochloride (EDC) to form AMBA-gelatin hydrogel. Like gelatin alone, AMBA-gelatin can maintain the colloid form at room temperature. Further, AMBA can be polymerized and conjugated with APS treatment onto a gelatin graft, for example, a gelatin sponge such as Gelfoam® (FIG. 2C). Conductivity measurement showed AMBA-gelatin had significantly enhanced conductivity compared with gelatin (FIG. 2B). Conductivity measurement also showed AMBA conjugated with Gelfoam® (AMBA-Gelfoam) had significantly enhanced conductivity compared with either Gelfoam® (Gelfoam) or AMBA mixed with Gelfoam® (AMBA+Gelfoam) (FIGS. 2C and D).

Figure 7A:
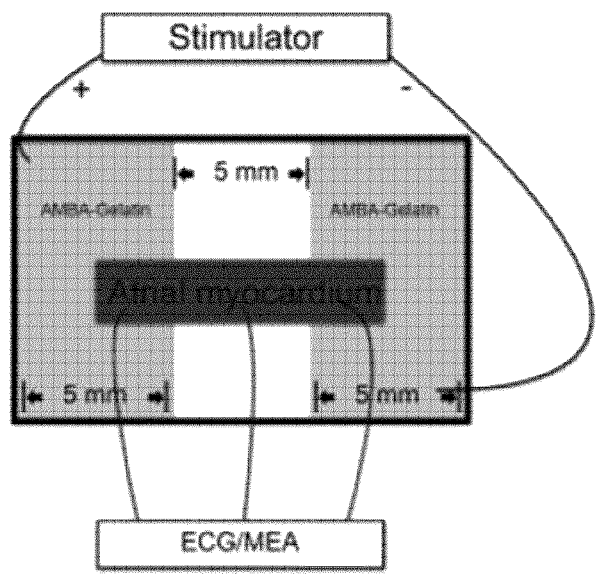
FIG. 7(a) Schematic of the in-vitro experiment.
Figure 7B:
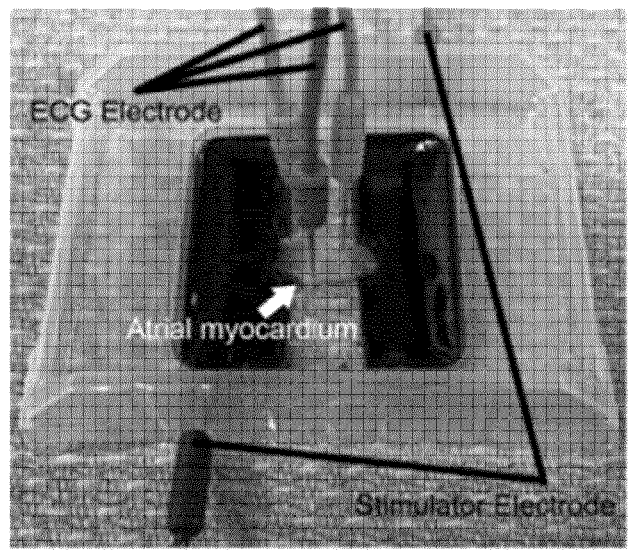
FIG. 7(b) Photograph of the assay outlined in (a) ECG was used to detect action potentials.
Figure 7C:
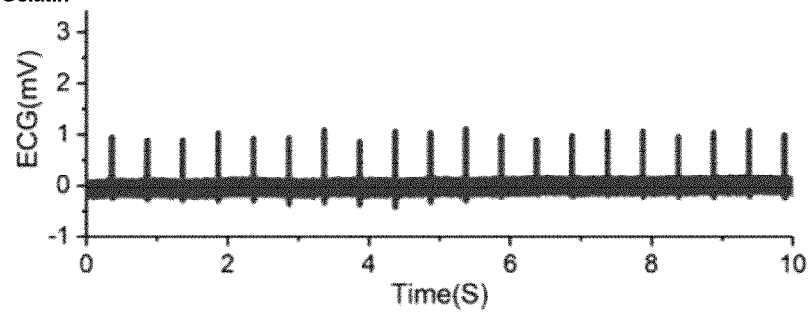
FIG. 7 shows 3-4-AMBA-gelatin converting current to cardiac bioelectricity and increasing myocardium reactivity to current stimulation.
FIG. 7(e) Photograph of the assay outlined in FIG. 7(a). Multielectrode array (MEA) was used to detect conductive velocity.
Figure 7D:
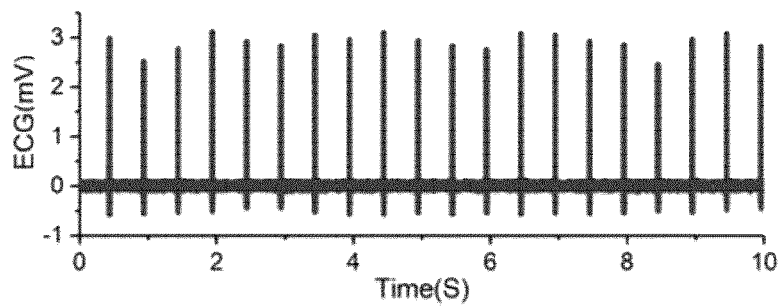
Figure 7E:
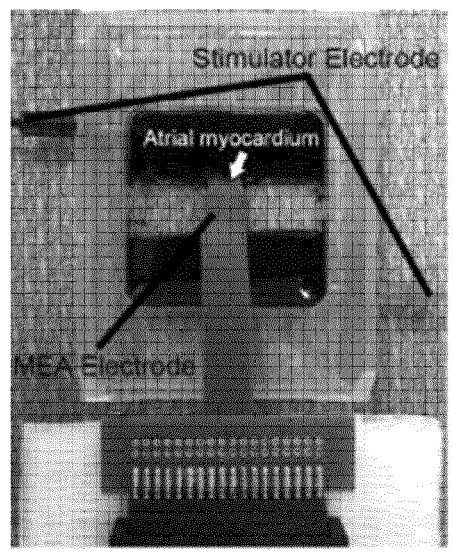
Figure 7F:
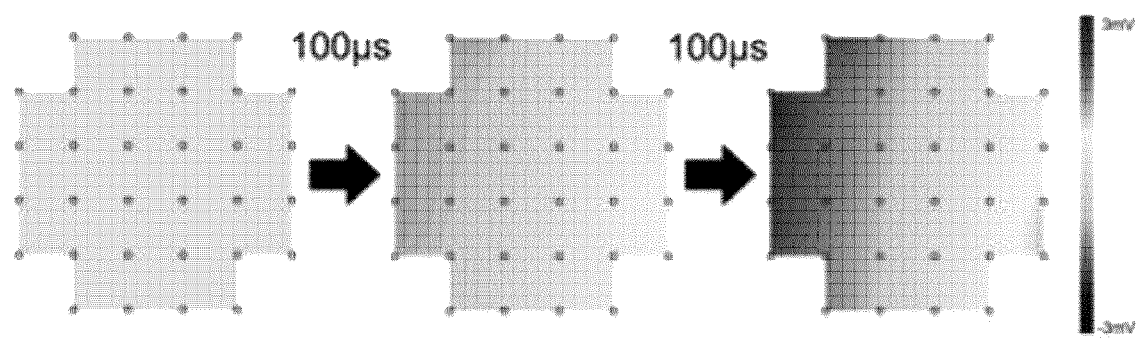
Figure 7G:
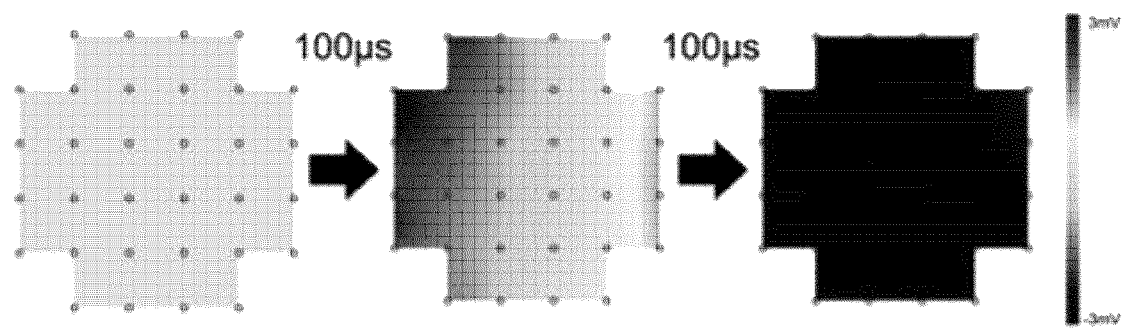
Figure 7H:
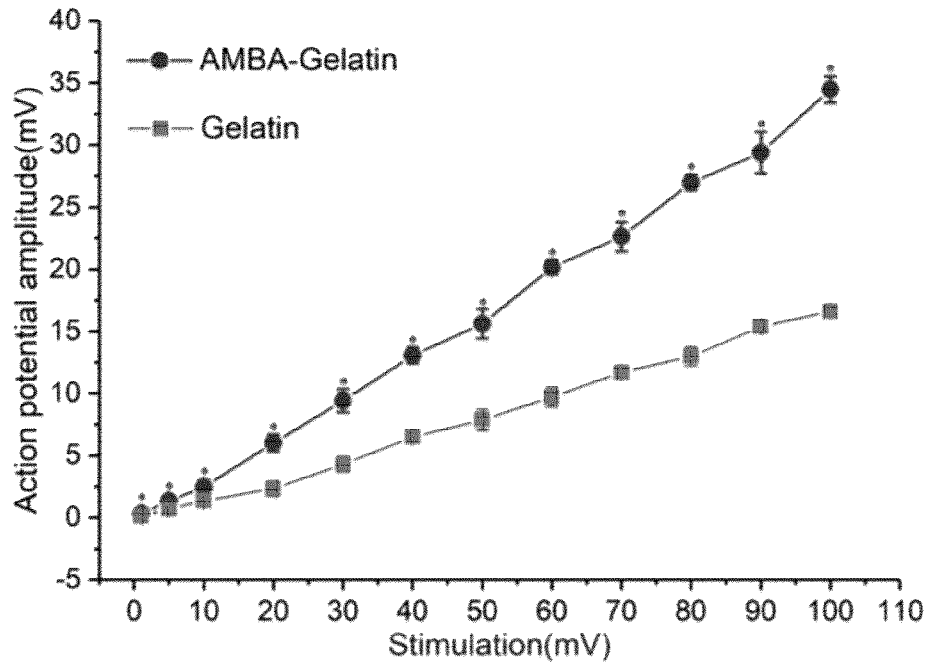
Figure 7I:
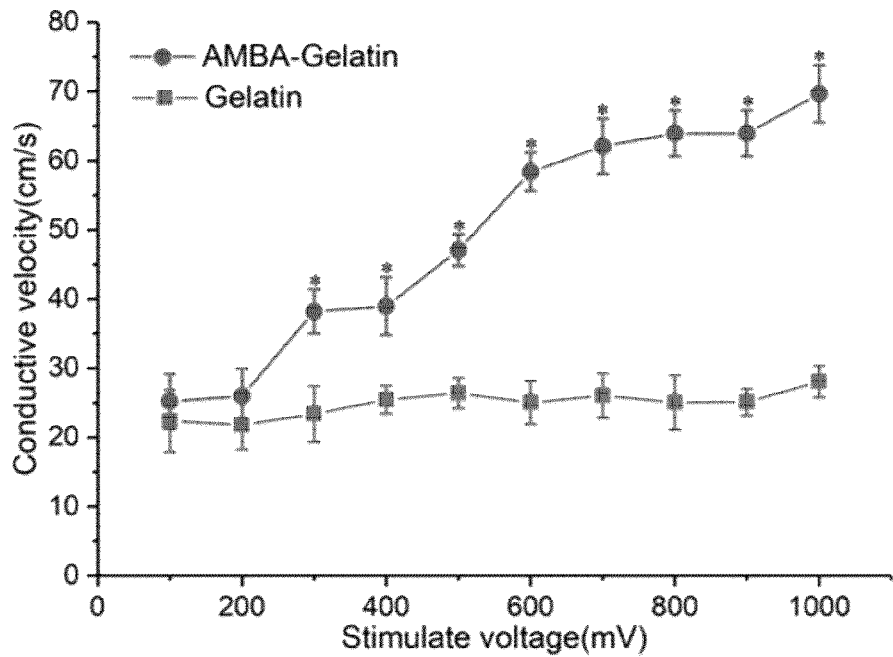

An in-vitro model for simulating the electrode-tissue interface with isolated atrial myocardium was developed to compare the conduction between AMBA-gelatin and gelatin (FIG. 7a). First, the action potential amplitude of the isolated atrial myocardium was detected under different stimulation voltages with ECG monitoring (FIG. 7b). It was found that myocardial action potential amplitude was significantly greater in AMBA-gelatin than gelatin (FIGS. 7c, 7d and 7h). Then the conductive velocity of the isolated atrial myocardium was detected at different stimulation voltages with MEA monitoring (FIG. 7e). The conductive velocity was significantly increased from 300 to 1,000 mV stimulation in the AMBA-gelatin group compared to gelatin alone (FIGS. 7g and 7i). These data suggest that the conductive AMBA-gelatin hydrogel displays significantly higher conductivity and improved conductive propagation than gelatin alone.

Figure 8A:
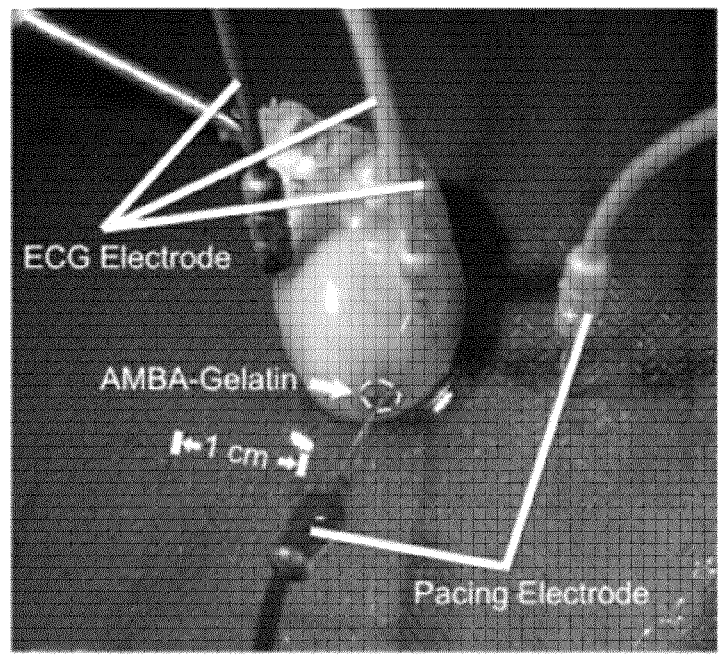
FIG. 8(a) Photograph of the Langendorff isolated rat heart model, isolated heart was placed on a mat which was painted with reference lines, a cathode electrode was inserted in the AMBA-gelatin area near the heart apex and an anode electrode was inserted in the Krebs-Henseleit buffer (KHB) about 1.5 cm away from the cathode electrode. ECG was used to record heart electrical activity.
Figure 8B:
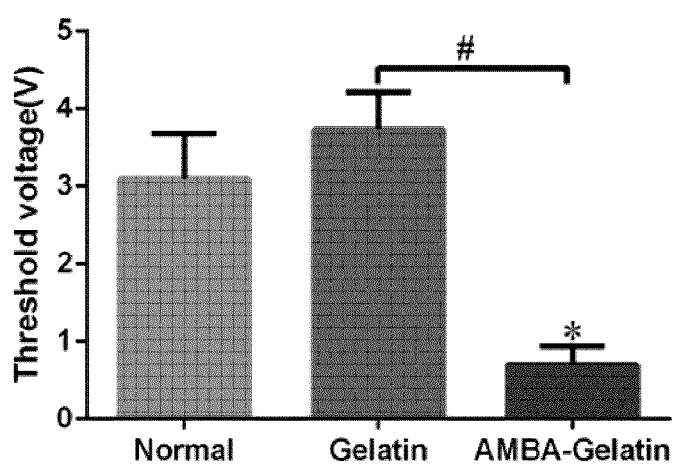
FIG. 8(b) AMBA-gelatin-electrode pacing showed significantly lower threshold voltage compared with normal pacing or Gelatin-electrode pacing (n=6/group, *$P<0.05$ compared with electrode, #$P<0.05$ compared with gelatin).
Figure 8C:
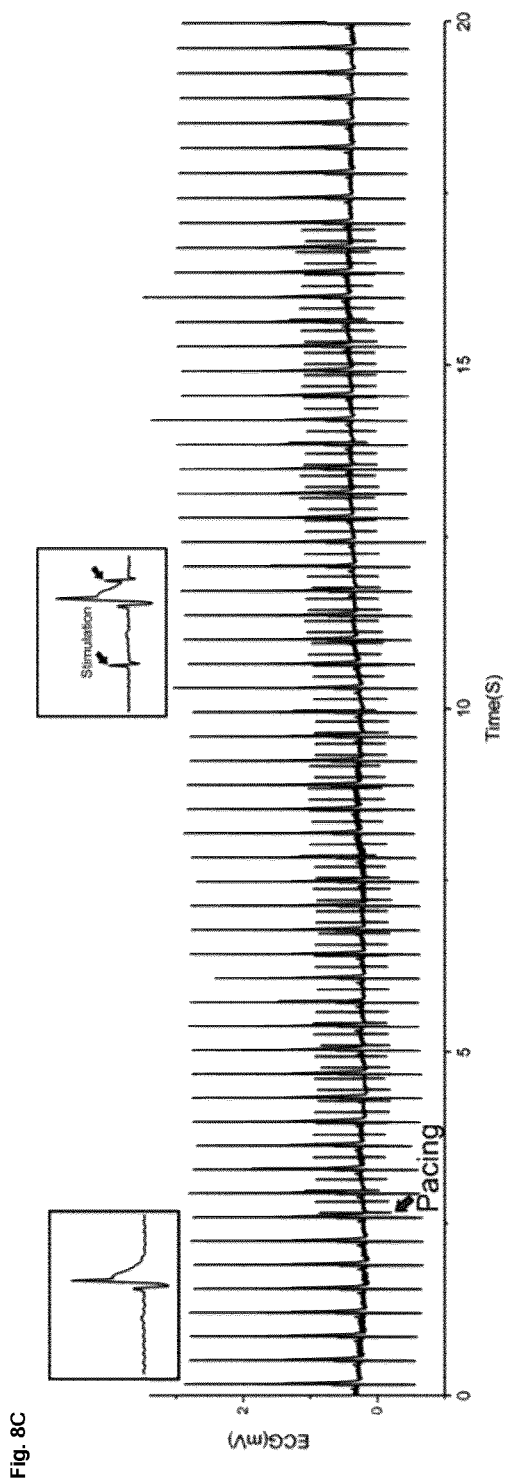
FIG. 8(c) Representative ECG traces under 0.5 v normal electrode pacing. Stimulation and cardiac rhythm were mutually independent. Details ECG trace was shown in the box.
Figure 8E:
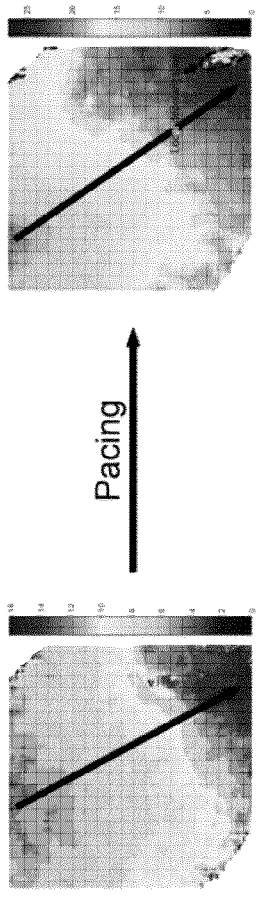
FIG. 8 shows 3-4-AMBA-gelatin decreased heart pacing threshold voltage in the Langendorff isolated rat heart model.
FIG. 8(f) Representative ECG traces under 0.5 v gelatin-electrode pacing, stimulation and cardiac rhythm were mutually independent. Detail of the ECG trace was shown in the box.
FIG. 8(i) Representative ECG traces under 0.5 v AMBA-gelatin-electrode pacing. Stimulation induced whole heart depolarization successfully and the heart was under pacing rhythm. Detail of the ECG trace is shown in the box.
Figure 8D:
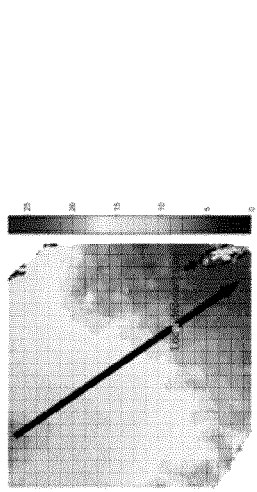

AMBA-Gelatin Hydrogel Decreased Cardiac Pacing Threshold Voltage in Adult Rat Heart To evaluate alteration of myocardial impedance and reduction of cardiac pacing threshold voltage after injection of AMBA-gelatin into the myocardium at pacing electrode site, the Langendorff apparatus was used to perfuse hearts and the hearts were beating in sinus rhythm (FIG. 8a). The pacing probe was placed in the left ventricle and 0.5V stimulation was used. The normal heart group showed a completely separated stimulation wave and heart rhythm (FIG. 8c). The optical mapping displayed a small local depolarization area at the site of electrode insertion (FIGS. 8d and 8e). In the gelatin group at 0.5V stimulation, the ECG also showed completely separated stimulation waves and heart rhythm tracings (FIG. 8f) and the optical mapping showed noise in the gelatin injection area, which reflected the low conductivity of gelatin (FIGS. 8g and 8h). In the AMBA-gelatin group, 0.5V stimulation was high enough to change the rhythm from autonomous cardiac rhythm to the pacing rhythm (FIG. 8i) and optical mapping results detected an ectopic pacemaker at AMBA-gelatin injection area under stimulation (FIGS. 8j and 8k). These data suggested that under 0.5V stimulation into the conductive biomaterial enhanced cardiac depolarization by reducing the pacing threshold. To further evaluate the lowest voltage necessary to induce heart depolarization in the 3 groups of the hearts, stimulating voltage was increased to identify the threshold to pacing heart (synchronization of pacing and autonomous heart rates). The results showed that AMBA-gelatin injection significantly reduced the cardiac pacing threshold voltage compared with normal electrode or electrode-gelatin pacing (FIG. 8b).

AMBA-Gelatin in the Myocardium Improved Pacing Electrophysiological Performance

Figure 9A:
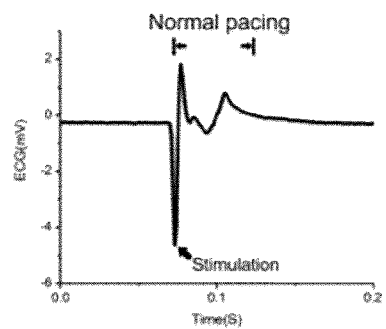
FIG. 9 shows 3-4-AMBA-gelatin improved pacing electrophysiological performance in the Langendorff isolated rat heart model.
FIG. 9(d) AMBA-gelatin-electrode pacing showed significantly decreased relative Q-T wave duration time compared with normal electrode pacing or Gelatin-electrode pacing (n=6/group, *P<0.05 compared with electrode).
FIG. 9(e) Representative 80% action potential duration (APD) map in optical mapping under direct electrode, gelatin-electrode and AMBA-gelatin-electrode with 5 v stimulation. Electrode, gelatin and AMBA-gelatin injection area are identified by arrows.
FIG. 9(f) normal electrode and gelatin-electrode with 5 v pacing showed significantly higher APD time compared with sinus rhythm while AMBA-gelatin pacing showed no differences (n=6/group, *P<0.05 compared with sinus).
FIG. 9(g) Representative whole heart conduction velocity map in optical mapping under normal electrode, gelatin-electrode and AMBA-gelatin-electrode with 5 v stimulation. Electrode, gelatin and AMBA-gelatin injection area are identified by arrows.
FIG. 9h, normal electrode and gelatin-electrode with 5 v pacing showed significantly lower conductive velocity compared with sinus rhythm while AMBA-gelatin pacing showed no differences (n=6/group, *P<0.05 compared with sinus).
Figure 9B:
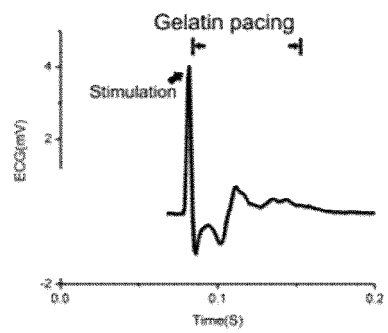
Figure 9C:
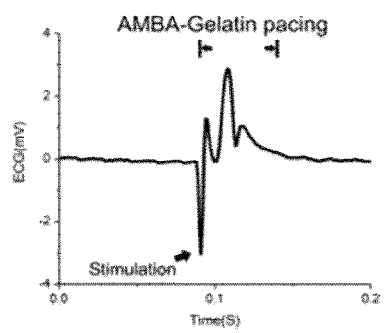
Figure 9D:
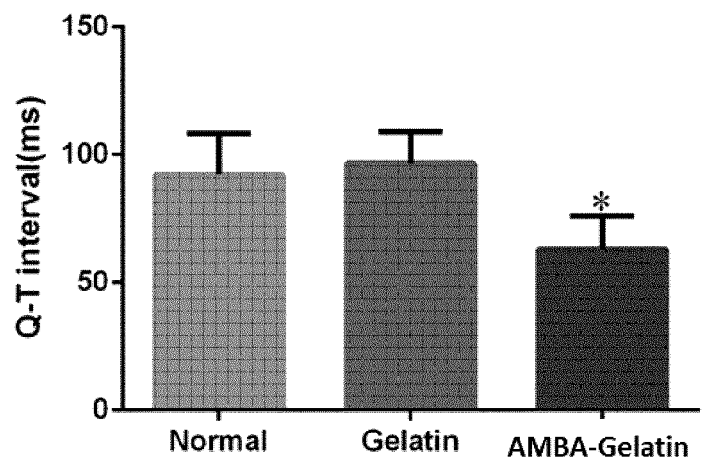

The normal hearts in Langendorff perfusion in normal, gelatin or AMBA-gelatin groups were consistently in a paced rhythm using 5.0V stimulation with 6 Hz and 4 ms duration. ECG data under pacing rhythm was analyzed for electrode (normal), gelatin and AMBA-gelatin groups (FIGS. 9a, 9b and 9c). The AMBA-gelatin group had significantly decreased Q-T duration compared with normal electrode and gelatin groups (FIG. 9d), which suggests a better coordinated contraction between left and right ventricles [23].

Figure 9E:
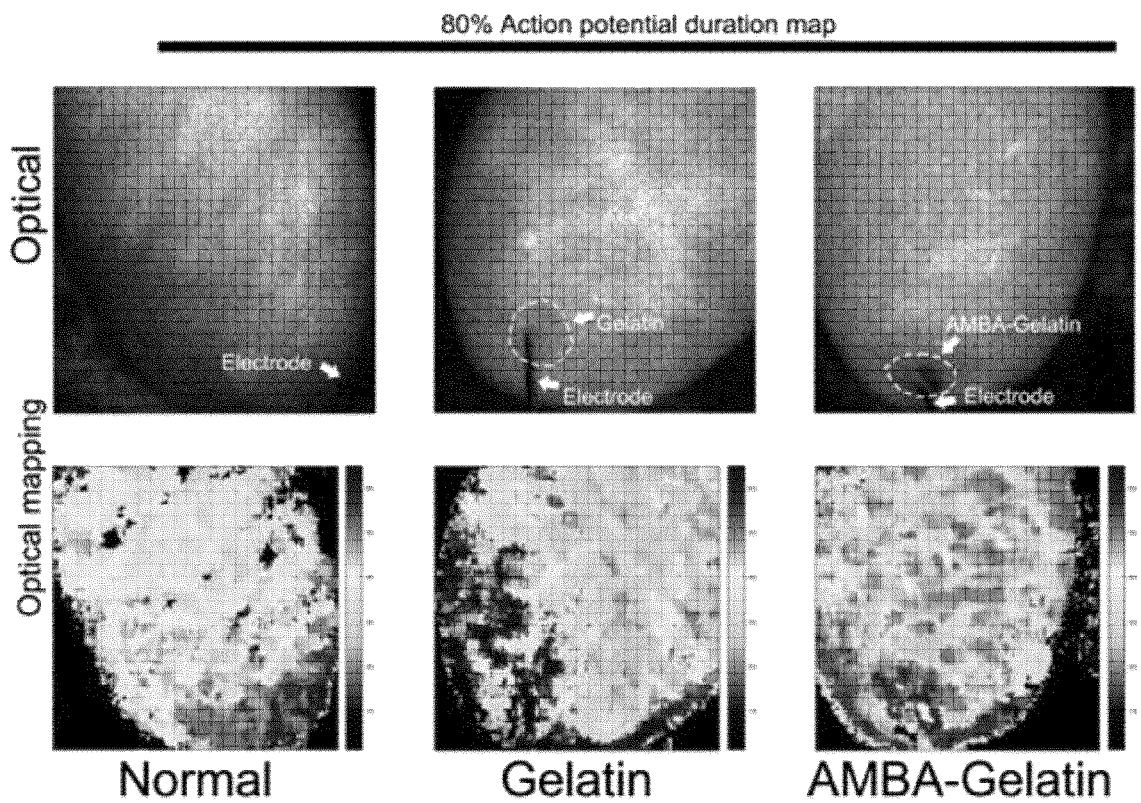
Figure 9F:
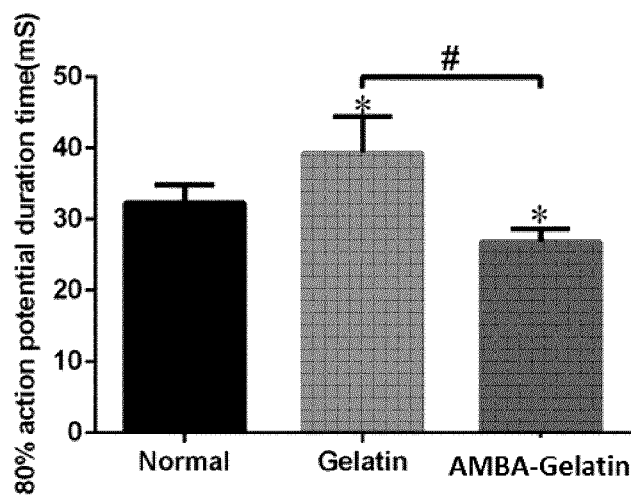

The optical mapping data were used for calculation of 80% action potential duration (80% APD) time. Representative optical images and 80% APD graphs in each group were shown in FIG. 9e. The optical mapping results confirmed the ECG findings, demonstrating that 80% APD time in the normal and gelatin groups were significantly longer than AMBA-gelatin group, while there were no significant differences in 80% APD time between sinus rhythm and AMBA-gelatin groups with 5.0V stimulation (FIG. 9f).

Figure 9G:
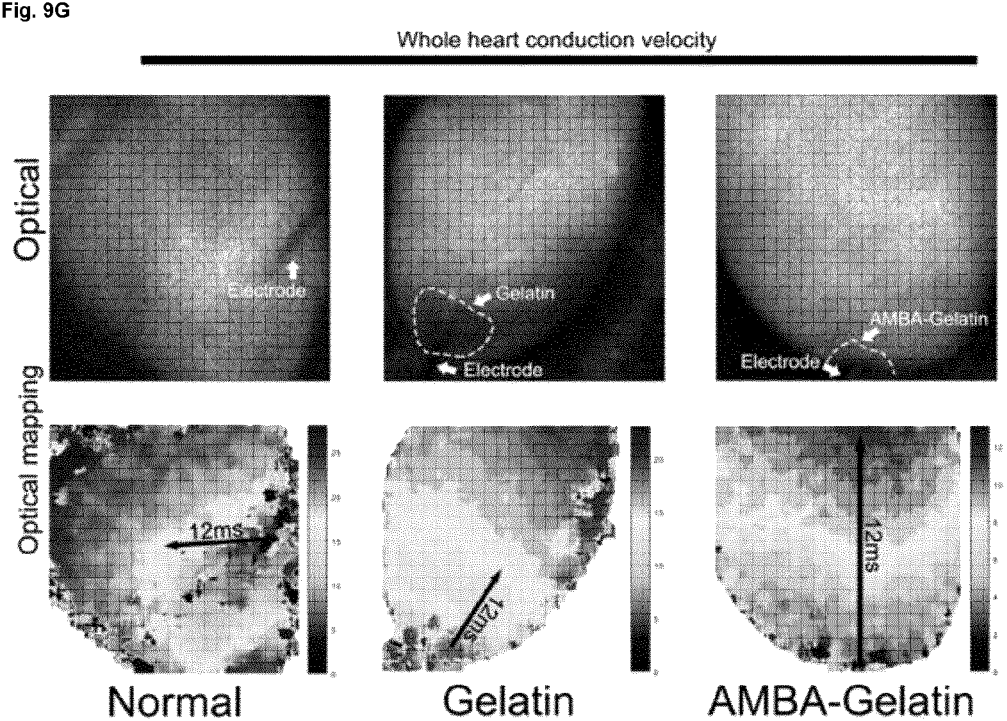
Figure 9H:
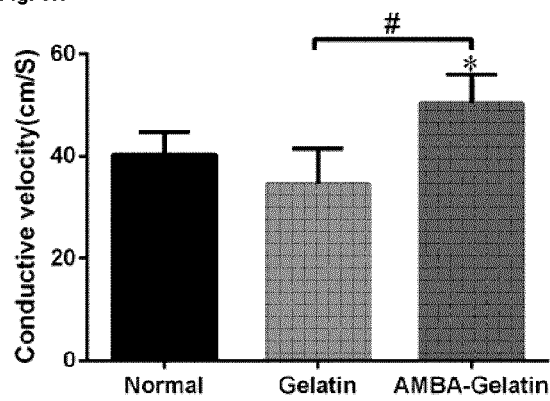

Optical mapping data also illustrated myocardial conductive velocity (CV) in the 3 groups. The conductive velocities in the normal myocardium and gelatin groups were significantly slower compared with sinus rhythm and AMBA-gelatin groups, while there were no significant differences in conductive velocity between sinus and AMBA-gelatin group during 5.0V stimulation (FIGS. 9g and 9h). These results indicated that AMBA-gelatin pacing was closer to physiological electrical conditions compared with normal electrode and gelatin pacing, which was reflected in similar Q-T interval, 80% APD time and CV compared with sinus rhythm.

Figure 10A:
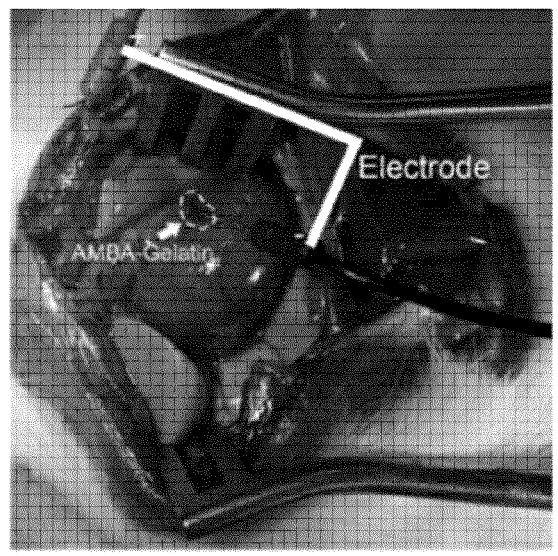
FIG. 10(a) Photograph of the AMBA-gelatin-electrode in vivo pacing model, cathode electrode was inserted in the AMBA-gelatin area near heart apex and anode electrode was inserted in the left side of the sternum subcutaneously.
Figure 10B:
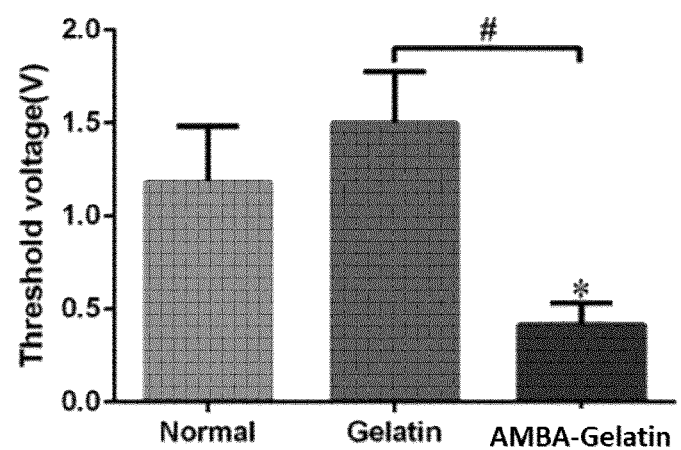
FIG. 10(b) AMBA-gelatin-electrode pacing showed significantly lower threshold voltage compared with normal electrode pacing or Gelatin-electrode pacing in vivo (n=6/group, *P<0.05 compared with electrode, #P<0.05 compared with gelatin).
Figure 10C:
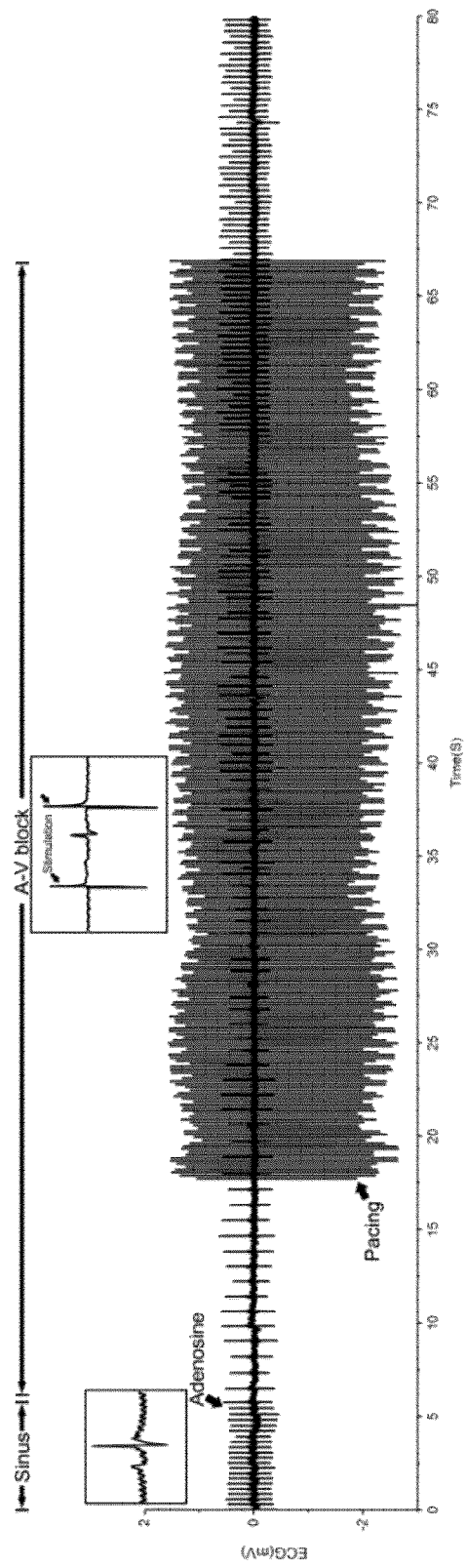
FIG. 10 shows AMBA-gelatin decreased heart pacing threshold voltage and pacing electrophysiological performance in vivo.
FIG. 10(i) AMBA-gelatin-electrode pacing showed significantly decreased relative Q-T wave duration time compared with normal electrode pacing and Gelatin-electrode pacing while Gelatin-electrode pacing showed increased Q-T wave duration time compared with normal electrode pacing. (n=6/group, *P<0.05 compared with electrode, #P<0.05 compared with gelatin).
Figure 10D:
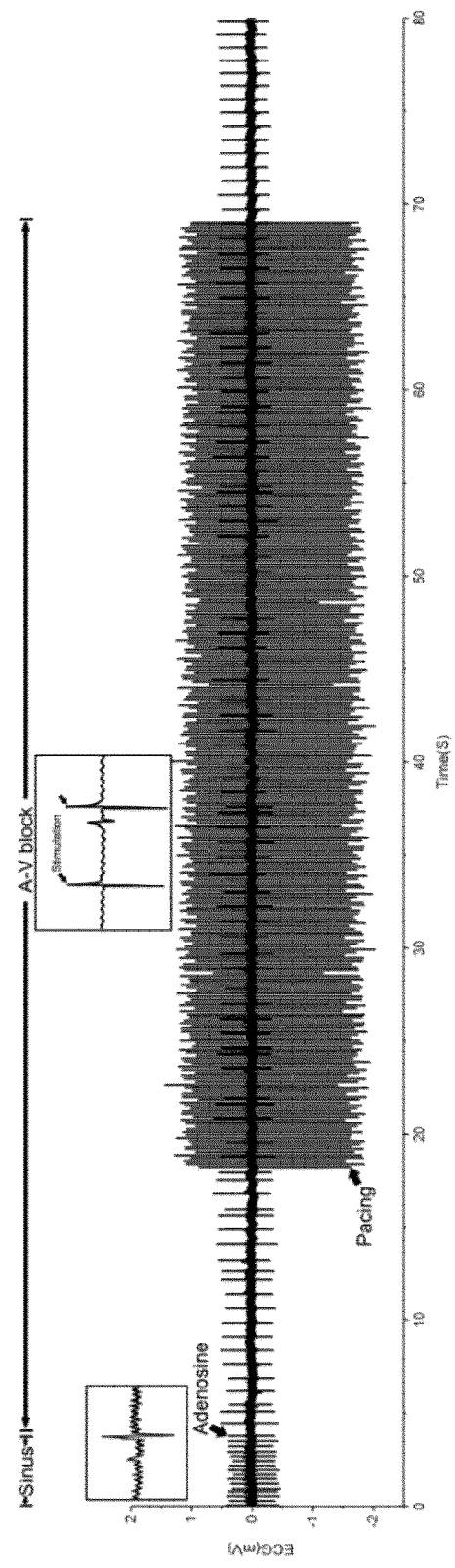
Figure 10E:
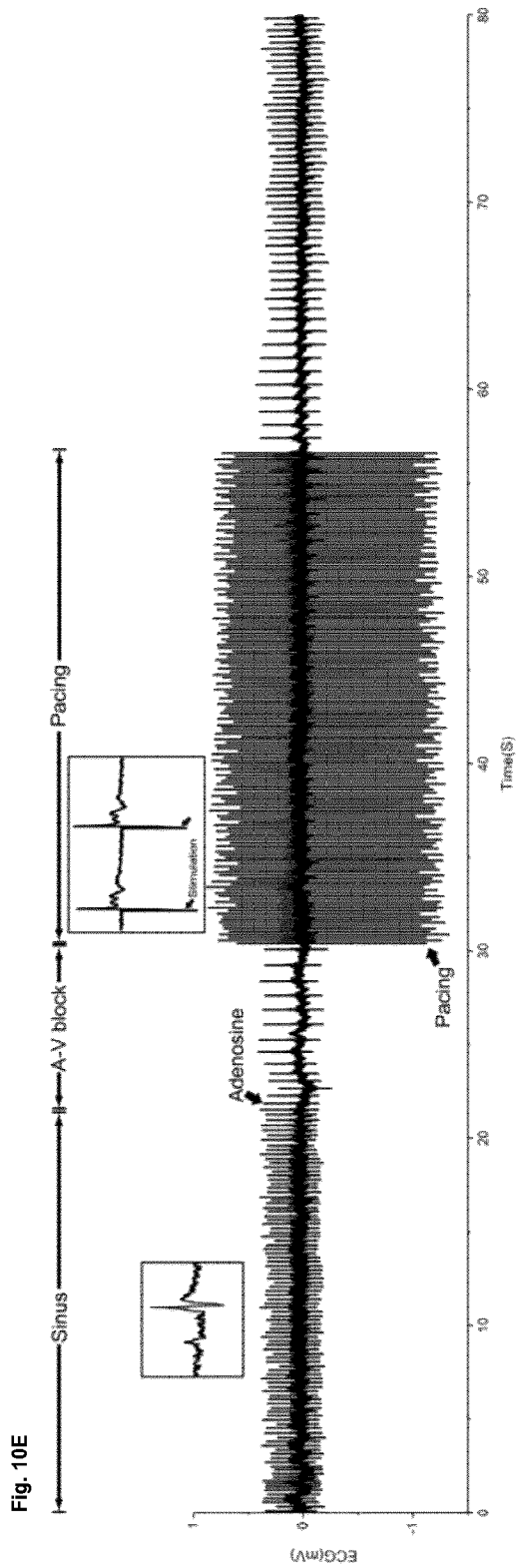
Figure 10F:
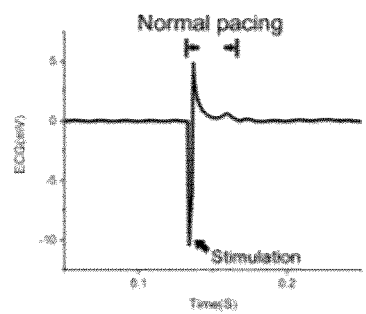
Figure 10G:
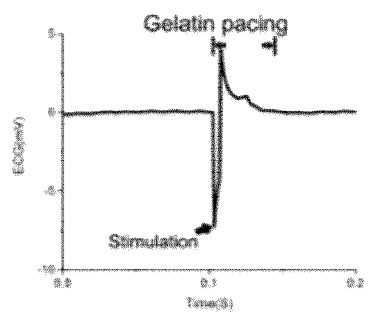
Figure 10H:
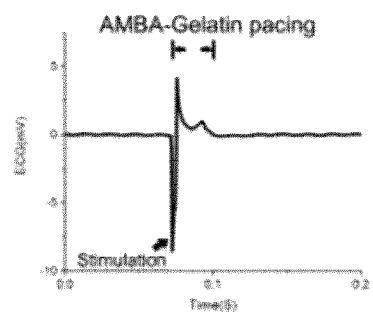
Figure 10I:
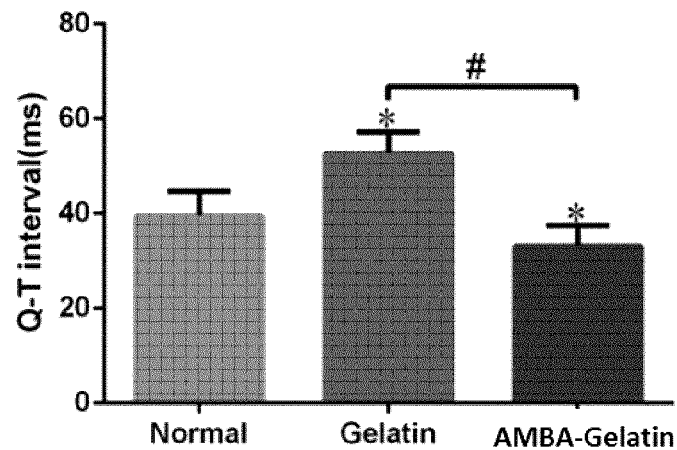
Figure 11:
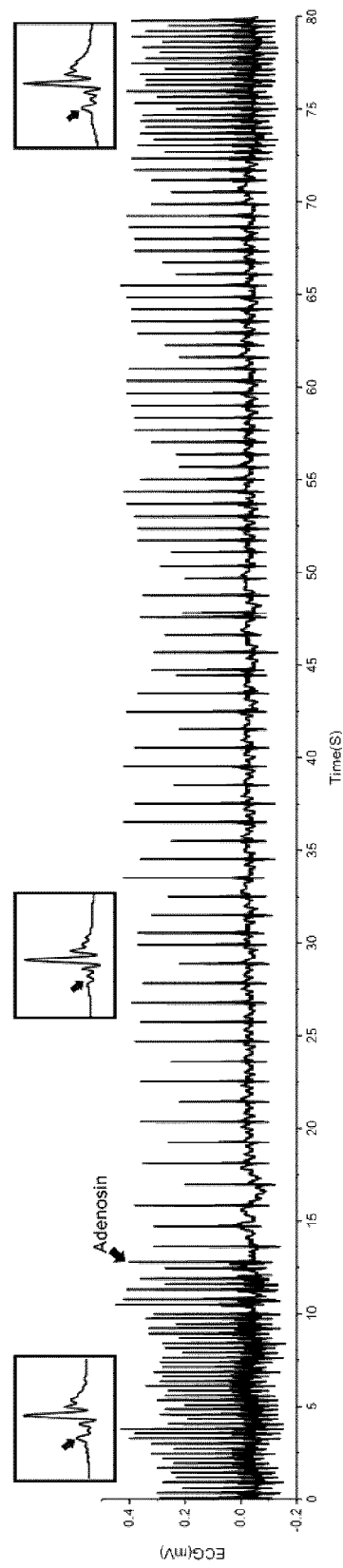
FIG. 11 shows adenosine induced atrioventricular block model. Representative ECG traces showed adenosine injection inhibited sinoatrial node electrical activity which induced an inverted P wave in ECG trace and that sinus rhythm spontaneously recovered tens of seconds after adenosine injection. Detail ECG trace is shown in the box and P wave is identified by arrows.

AMBA-Gelatin Hydrogel Reduced Pacing Threshold Voltage and Improved Pacing Electrophysiological Performance In Vivo To evaluate the pacing characteristics, adenosine (AD) was injected through inferior vena cava to decrease the heart rate in vivo (FIG. 10a). After AD injection, the sinus node was suppressed with a reversed P wave on ECG and a decreased heart rate (FIG. 11). Representative ECGs showed that electrode stimulation using 0.5V/6 Hz and 4 ms duration in normal tissue and gelatin group resulted in totally separated pacing tracings and autonomous rhythm while the heart rhythm changed to totally paced rhythm with an increased heart rate in the AMBA-gelatin group (FIGS. 10c, 10d and 10e, respectively). Statistic results showed pacing threshold voltage in AMBA-gelatin group was significantly decreased compared with normal electrode and gelatin group (FIG. 10b). The Q-T interval analysis was performed in normal, gelatin and AMBA-gelatin groups (FIGS. 10f, 10g and 10h, respectively). The Q-T duration was significantly increased in normal and gelatin group compared with the AMBA-gelatin group (FIG. 10i). These data suggests that AMBA-gelatin hydrogel injection reduces the pacing threshold voltage and improves the pacing electrophysiological performance in vivo, which corroborates with the findings in Langendorff isolated rat heart model.

Figure 12:
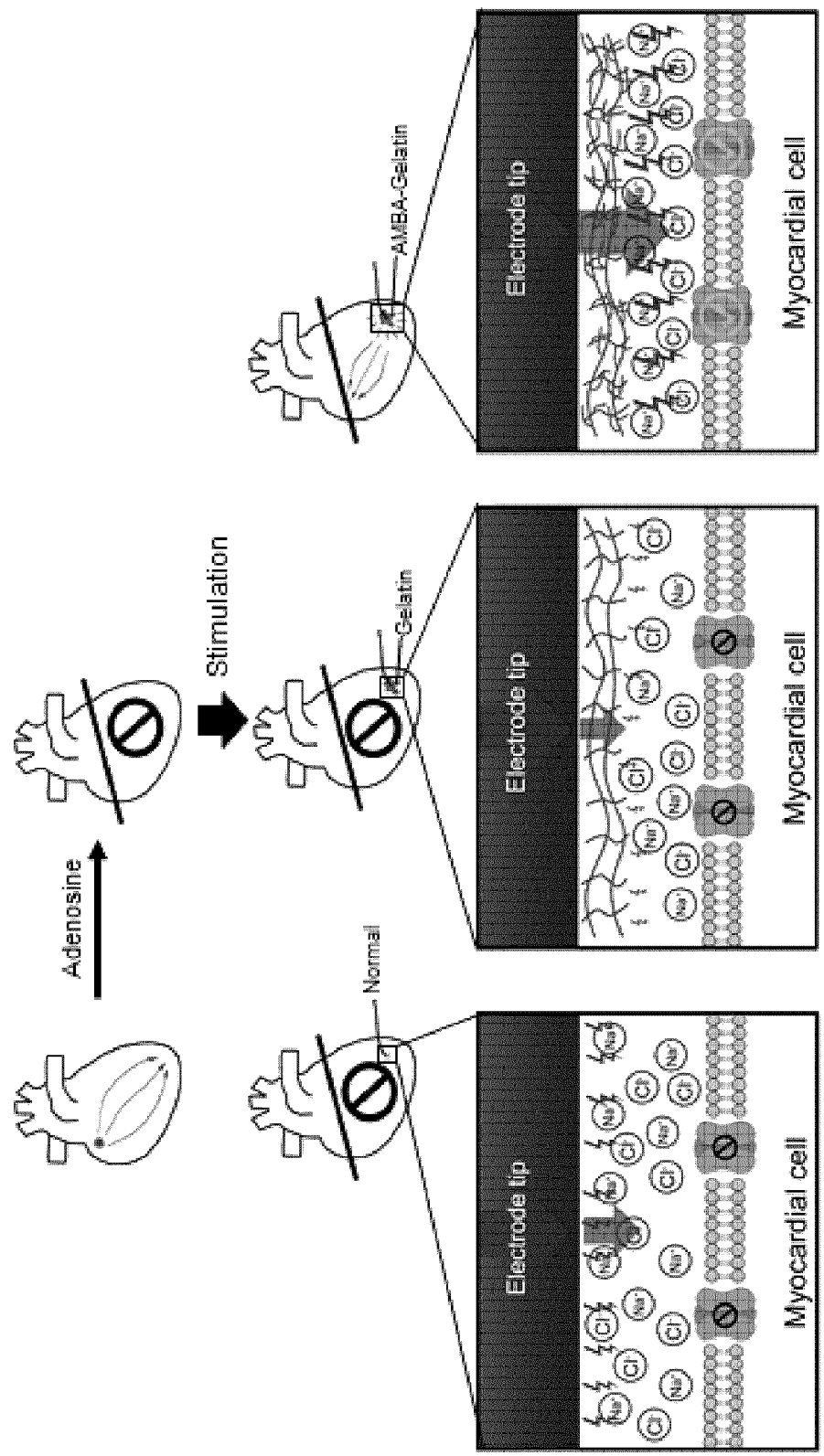
FIG. 12 shows a central picture for the in vivo experiment. Under in vivo experiment, adenosine was used to build an atrioventricular block model and AMBA-gelatin-electrode pacing induced whole heart depolarization successfully while normal and gelatin-electrode pacing failed.

Taken together, AMBA-gelatin may reduce cardiac pacing threshold voltage and improves pacing electrophysiological performance by providing a higher electrode-tissue interface and may have reduced the distance between electrode and cell membrane (FIG. 12).

A conductive biomaterial of AMBA-gelatin hydrogel was developed and found to reduce cardiac pacing threshold voltage. The conductive biomaterial may be useful in reducing pacemaker energy consumption.

During the clinical application, the battery life of pacemaker becomes a functional issue when the initiation of myocardial depolarization must overcome an increased impedance due to local fibrosis. Several new techniques have been developed, such as reducing electrode surface area [24], adopting microporous structure in the cathode electrode [17], use of new materials [25-27] and introducing steroid-eluting leads to inhibit local fibrosis [28]. Application of these techniques has reduced the pacemaker threshold voltage [29, 30], and prolonged pacemaker battery life in the past decades [31, 32]. However, energy consumption of current pacemakers is still high and most patients need a second operation to replace the exhausted battery [33].

It is known that electrode-myocardial tissue interface plays an important role in cardiac pacing. With external pacing, the current at the electrode tip must generate an electric field. If the electric field at the myocardium cells reaches its threshold voltage, then it opens the voltage-gated sodium channels on the cell membrane and generates an action potential [28]. As myocardial fibrosis increases the tissue impedance reduces myocardial conductivity and delays electrical signal propagation contributing to higher pacing threshold [18]. Reduced myocardial tissue impedance can decrease the depolarization threshold. Injecting AMBA-gelatin hydrogel into the electrode-tissue interface has been shown to significantly increase myocardial cell membrane voltage compared with the control groups, by reducing cardiomyocyte impedance.

The ex vivo study exhibited a pacing threshold voltage for AMBA-gelatin less than 1 v and 3-4 folds lower than the Control or gelatin pacing electrodes. Similarly, the in vivo AVB study showed that the threshold for AMBA-gelatin was less than 0.5 v and was ~3 fold lower than Control or gelatin pacing electrodes. Both ex vivo and in vivo data showed that the pacing threshold voltage was less than current clinically used 1.5 v [29, 30]. These data suggest that AMBA-gelatin pacing may significantly reduce the threshold, thereby decreasing the energy consumption.

Previous studies found that the threshold voltage significantly increased when the distance between electrode surface and cell membrane was longer than the electrode geometric radius [34]. Currently, the distance from the electrode surface to the cell membrane was significantly decreased by injecting AMBA-gelatin hydrogel to the electrode-tissue interface as illustrated in FIG. 12. This creates a more intense electric field on cell membrane which helps to reduce the threshold.

When conductive biomaterial was created, it was found that AMBA cannot be used for direct injection into the myocardial tissue because it is difficult to gel and has poor biocompatibility. To enhance biocompatibility and increase viscosity or gel formation, AMBA was conjugated to gelatin, a natural protein derived from collagen.

The pacing electrophysiology in healthy rats was also investigated and it was found that pacing electrophysiological performance was closer to physiological electrical condition for AMBA-gelatin compared with Control or gelatin pacing electrodes. The data showed that AMBA-gelatin injection reduced the QT duration and 80% APD time compared with normal electrode pacing. Additionally, the whole heart conduction velocity under AMBA-gelatin pacing was significantly increased compared with normal electrode pacing. The QT interval represents ventricular electrical depolarization and repolarization. Prolonged QT intervals are usually the result of intraventricular conduction delays and may contribute to progressive heart failure. The improved cardiac conduction and shortened QT intervals with AMBA-gelatin pacing may have clinical application in reducing ventricular dysfunction and progressive heart failure as well as in cardiac pacing.

Example 5—AMBA-Gelatin Hydrogel Improved Electrical Conductivity in Fibrotic Scar Tissue Methods:

Myocardial Infarction and Biomaterial Injection

Adult Sprague Dawley (SD) rats (230-260 g) were purchased from Charles River Laboratories (Saint-Constant, QC, Canada). All animal protocols and procedures were approved by the Animal Care Committee of the University Health Network. Experimental procedures in the animal studies were performed in accordance to the Guide for the Care and Use of Laboratory Animals (NIH, 8th Edition, 2011). Rats were mechanically ventilated and anesthetized with 2% isoflurane. A left lateral thoracotomy was made to expose the heart and the left anterior descending coronary artery was ligated to create a myocardial infarction (MI). The chest was then closed and animals were given buprenorphine (0.05 mg/kg) for analgesia. All animals were randomized into saline (n=12), Gelatin (n=12), or AMBA-Gelatin (n=12) injection groups. One week post MI, a second thoracotomy was performed to access the heart, where the ventricular scar was visualized as a white-grey area on the anterior wall of the left ventricle. 100 μL of saline, Gelatin, or AMBA-Gelatin was injected into the one scar and two border regions using a 28-gauge needle (BD Biosciences, Mississauga, ON). The chest was then closed and animals were given buprenorphine (0.05 mg/kg) for analgesia. All animals were sacrificed twelve weeks after biomaterial injection for optical mapping experiments.

Cardiac Electrophysiology

An eight-lead catheter ECG recording method and microelectrode array (MEA) was used to evaluate global and regional cardiac surface action potentials.

Telemetric ECG

ECG recordings were acquired from conscious, freely mobile animals using a Millar telemetry system (Millar Inc., Houston, Tex.). All recordings were obtained over a 24-hour period. Recordings were obtained from animals injected with AMBA-Gelatin or Gelatin at 12 weeks post-injection. All ECG traces were evaluated by a blinded cardiologist using Histogram software (Millar Inc.), who determined the total number and frequency of arrhythmic events including single and multiform premature ventricular contractions (PVCs), as well as non-sustained and sustained ventricular tachycardia (VT). In accordance with the Lambeth convention guidelines [21], VT was defined as a run of four or more PVCs, and sustained VT as a fast ventricular rhythm of >15 beats.

Programmed Electrical Stimulation

Programmed electrical stimulation (PES) studies were performed 12 weeks post-injection using methods modified from Nguyen et al. [22]. In brief, each animal was mechanically ventilated and anesthetized with 2% isoflurane. Surface ECGs were recorded using a 27 gauge subcutaneous electrode connected to a computer through an analog-digital converter for monitoring and subsequent offline analysis (Lab Chart 6 Pro, AD Instruments). A midline incision was made in the sternum, the chest was opened and the epicardial surface of the heart exposed. Two epicardial stimulating electrode needles (Millar Inc.) were inserted into the normal right ventricular myocardium. PES studies were then performed using an isolated stimulator-generator (STG-4002, Multichannel Systems, Germany). Standard clinical PES protocols, including burst (120 ms cycle length), single (70 ms cycle length), double (60 ms cycle length), and triple (50 ms cycle length) extra stimuli applied under spontaneous rhythm was employed. The heart was challenged three times with the train of eight or followed by the single extra-stimulus. If no PVC was induced, this procedure was repeated to apply three challenges with double and, if necessary, triple extra stimuli. The PES protocols were stopped if sustained (≤15 VT) or non-sustained VT was induced or until the protocol was exhausted. PVC and VT were induced in all infarcted animals with the application of a train of eight conditioning stimuli only or up to a triple extra stimulus. Arrhythmia susceptibility was determined using an inducibility quotient as follows: hearts with no PVCs or VT received a score of 0; non-sustained PVCs or VT (≤15 beats) induced with three extra stimuli were given a score of 1; sustained PVCs or VT (>15) induced with three extra stimuli were given a score of 2; non-sustained PVCs or VT induced with two extra stimuli were given a score of 3; sustained PVCs or VT induced with two extra stimuli were given a score of 4; non-sustained PVCs or VT induced with one extra stimulus were given a score of 5; sustained PVCs or VT induced with one extra stimulus were given a score of 6; sustained or non-sustained PVCs or VT induced after the train of eight were given a score of 7; asystole after termination of pacing was given a score of 8. The higher the score, the greater the arrhythmia inducibility [22].

Optical Mapping

At the 12-week end point, animals were euthanized and their hearts were stopped using a cardioplegic solution, and perfused using the Langendorff (120142, Radnoti, Monrovia, Calif.) technique (saline: n=6, Gelatin: n=6, AMBA-Gelatin: n=6). Hearts were perfused on ice with cardioplegic solution and voltage-sensitive dye (di-4-ANEPPS, D1199, Life Technologies) for 10 min. Electrical conduction was measured using an electron-multiplied charge-coupled device camera system (Evolve 128, Photometrics, Tucson, Ariz.), and isochronal maps were created. The videos were analyzed using Brainvision software (Brainvision Inc. Tokyo, Japan).

Cardiac Left Ventricular Function

Cardiac function was evaluated using echocardiography (echo, Vivid7, General Electric Healthcare) before infarction (0), at the time of biomaterial injection, and 2 and 4 weeks after injection. The following parameters were calculated by echo (n=6/group): left ventricular internal systolic dimension (LVIDs), left ventricular (LV) internal diastolic dimension (LVIDd), percentage of fractional shortening (LVFS) and percentage of ejection fraction (LVEF).

Statistical Analysis

Data are expressed as mean±standard deviation. Analyses were performed using GraphPad Prism software (v.6.0), with the critical α-level set at $p<0.05$. Student's t-tests were used for comparisons of means between two groups and comparisons of means among three or more groups were performed using ANOVA. For the ECG and echocardiographic analyses, which evaluated the same animals at different time points, repeated-measures ANOVA was employed. When the ANOVA F values were significant, differences between groups were determined using Tukey's post-hoc tests.

Results

The Conductive Biomaterial Enhanced Fibrotic Scar Tissue Field Potential Amplitude and Electrical Impulse Propagation with Reduced Myocardial Fibrotic Tissue Resistivity The effect of the conductive biomaterial on the electrical activity and tissue resistance of cardiac scar/fibrotic tissue in vivo was evaluated using a rat MI model. Four weeks post-injection, a 36 lead flexible microelectrode array (MEA) was employed to evaluate regional electrical field potential and detect the electrical impulse propagation across scar area (FIG. 13A). AMBA-Gelatin-injected infarcted hearts had greater scar field potential amplitude compared with infarcted hearts injected with gelatin. (FIGS. 13B & C, N=6/group).

To evaluate the biological conductive properties of the conductive biomaterial, at 4 weeks post-injection, 8-lead catheters were employed to measure global cardiac surface field potential amplitude during contraction, with 2 leads placed in normal myocardium, 2 leads in the border zone, and 2 leads in the fibrotic scarred area (FIG. 13D-F). AMBA-gelatin (-injected hearts had the highest scar field potential amplitude ratio (scar amplitude/remote amplitude) compared with infarcted hearts injected with gelatin ($p<0.01$, N=5/group). These results suggest that AMBA-gelatin injection improved electrical activity in fibrotic scar tissue.

Conductive Biomaterial in AMBA-Gelatin-Injected Infarcted Rat Heart Reduced the Rate of Spontaneous Arrhythmias after MI To relieve the concern with the injection of the conductive polymer into the infarct scar to increase the susceptibility to cardiac arrhythmias, the ambulatory telemetric ECG recordings were obtained at 4 weeks after injecting the conductive material into the fibrotic scar. Within 72 hours continuous recording, the infarcted animals showed consistent preventricular contractions (PVCs) (FIG. 14A), but the AMBA-Gelatin) group had the lower rate of PVCs per hour (FIG. 14, p<0.05 vs. gelatin, N=5).

Injection of Conductive Biomaterial Reduced the Induced Arrhythmia

To investigate the sensitivity of the infarcted hearts to the cardiac arrhythmias, the standard clinical method, programmed electrical stimulation (PES), was used to induce arrhythmias. At 4 weeks post biomaterial injection, the rat hearts were subjected to PES to determine the effects of the biomaterial injections on PVC induction (FIG. 14C). When challenged with PES, arrhythmia susceptibility based on the inducibility quotient was significantly lower in rats injected with AMBA-gelatin compared to those injected with gelatin suggesting lesser arrhythmic susceptibility (FIG. 14D, p<0.01, N=5/group).

Injection of Conductive Biomaterial Enhanced Global Fibrotic Scar Tissue Field Potential Amplitude, Improved Conduction Velocity In Vivo To directly assess left ventricle electrical signal conduction velocity, the optical mapping technique in biomaterial-injected animals was employed. Hearts from healthy rats (without MI), and those injected with gelatin alone or AMBA-gelatin post-MI were excised at the end of the study (at 4 weeks) and Langendorff-perfused. A voltage-sensitive dye (di-4-ANEPPS) was used to evaluate electrical impulse conduction velocity across the normal and infarct scar regions in all groups (FIG. 14E-G). FIG. 5H shows that gelatin-injected hearts had significantly decreased longitudinal conduction velocity in comparison with normal heart. However, the longitudinal conduction velocity in AMBA-gelatin-injected heart was close to the normal heart and was significantly greater than in gelatin-injected hearts (FIG. 14H, p<0.01, N=6/group). These results suggest that AMBA-gelatin injection improves the cardiac electrical signal conduction after injury.

Figure 15A:
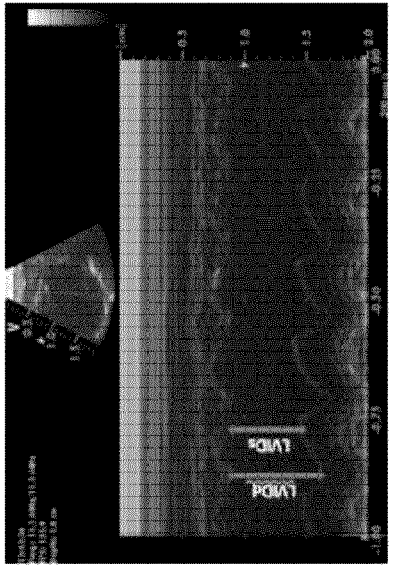
FIG. 15(A) Left anterior descending coronary artery (LAD) ligation was performed to induce myocardial infarction (MI) in rats. Gelatin or AMBA-gelatin) were injected into the ligated area one week later. Cardiac function were evaluated by echocardiography at 4 weeks post MI. Representative M-mode echo images 4 weeks after MI demonstrated that the AMBA-gelatin group had smaller left ventricular internal systolic dimension (LVIDS) than the Gelatin group. When comparing mean fractional shortening FIG. 15(B) and (LVIDS FIG. 15(C)) between the experimental groups, AMBA-gelatin injection showed significant improvement in comparison with the gelatin alone group. LVIDd=left ventricular internal diastolic dimension.
Figure 15B:
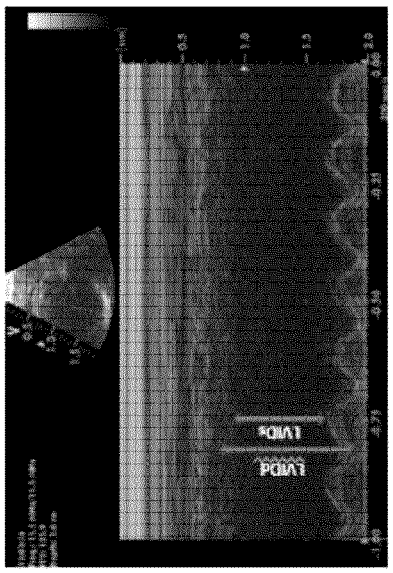
FIG. 15 shows AMBA-gelatin injection improved cardiac function following MI.
Figure 15C:
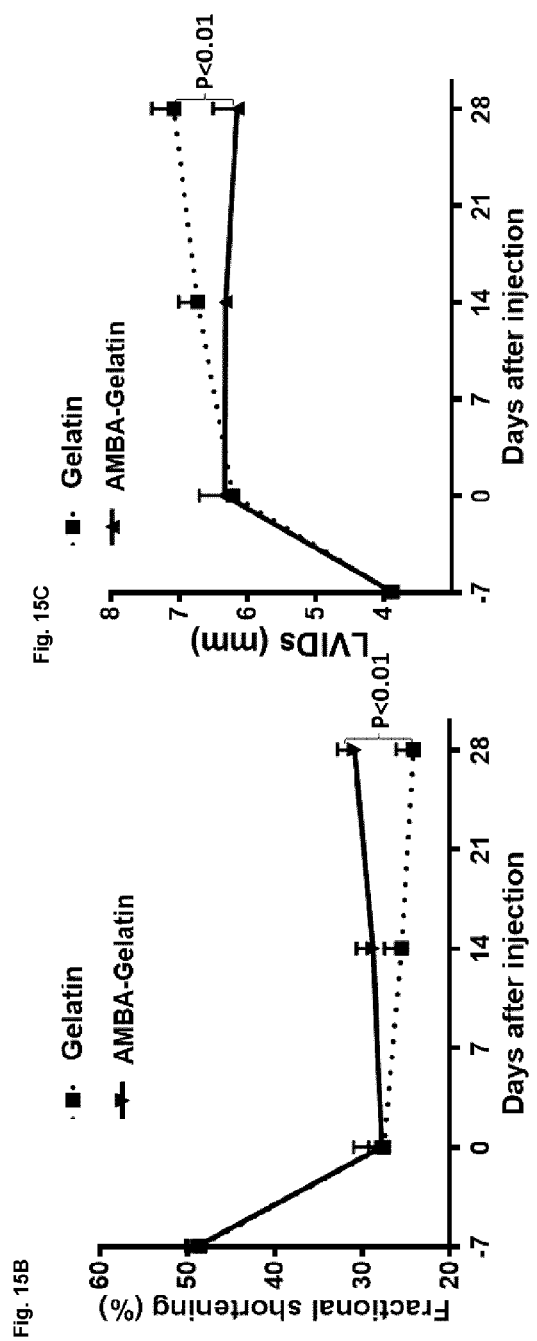

Conductive Biomaterial Improved Presumed Synchronized Contraction and Preserved Cardiac Function Following MI Hearts injected with AMBA-gelatin or gelatin was assessed using echocardiography (Echo) on day −7 up to +28 days relative to the biomaterial injection (FIG. 15). All groups showed reduced left ventricular fractional shortening (LVFS) and increased LV internal systolic dimensions (LVIDs) on day 0 relative to baseline, but there were no significant differences between the two groups. The gelatin control group exhibited increased LVIDs and decreased FS between day −7 up to +28. However, AMBA-gelatin improved these parameters at 28 days post-injection which showed significantly greater FS with lower LVIDs than gelatin control (p<0.01, N=6). Lower LVIDs suggested reduction of adverse heart remodeling probably due to improved synchronized contraction.

Example 6

The AMBA-gelatin sponge was prepared as described in Example 1. The AMBA gelatin sponge and a regular gelatin sponge (no AMBA polymer) were each submerged in cardiac cell culture media and cardiomyocytes were loaded onto each of the sponges.

Cells were grown for about 2 weeks and tested for synchronization of contractions by measuring calcium release using imaging analysis. It was found that cells grown on the AMBA-gelatin were synchronized whereas the cells grown without AMBA-gelatin polymer were not synchronized While this disclosure has been particularly shown and described with reference to example embodiments thereof, it will be understood by those skilled in the art that various changes in form and details may be made therein without departing from the scope of the invention encompassed by the appended claims.

All publications, patents and patent applications are herein incorporated by reference in their entirety to the same extent as if each individual publication, patent or patent application was specifically and individually indicated to be incorporated by reference in its entirety.

REFERENCES

1. Cingolani E, Ionta V, Cheng K, Giacomello A, Cho H C, Marbán E. Engineered electrical conduction tract restores conduction in complete heart block: from in vitro to in vivo proof of concept. J Am Coll Cardiol. 2014 Dec. 23; 64(24):2575-85.
2. Etsadashvili K, Hintringer F, Stühlinger M, Dichtl W, Spuller K, Antretter H, Hangler H, Pachinger O, Roithinger F X, Berger T. Long-term results of high vs. normal impedance ventricular leads on actual (Real-Life) pacemaker generator longevity. Eur Pacing Arrhythm Card Electrophysiol J Work Groups Card Pacing Arrhythm Card Cell Electrophysiol Eur Soc Cardiol. 2009 February; 11(2):200-5.
3. Li R A. Gene- and cell-based bio-artificial pacemaker: what basic and translational lessons have we learned? Gene Ther. 2012 June; 19(6):588-95.
4. Miake J, Marbán E, Nuss H B. Biological pacemaker created by gene transfer. Nature. 2002 September 12; 19(6903):132-3.
5. Tse H-F, Xue T, Lau C-P, Siu C-W, Wang K, Zhang Q-Y, Tomaselli G F, Akar F G, Li R A. Bioartificial sinus node constructed via in vivo gene transfer of an engineered pacemaker HCN Channel reduces the dependence on electronic pacemaker in a sick-sinus syndrome model. Circulation. 2006 Sep. 5; 114(10):1000-11.
6. Xue T, Siu C-W, Lieu D K, Lau C-P, Tse H-F, Li R A. Mechanistic role of I(f) revealed by induction of ventricular automaticity by somatic gene transfer of gating-engineered pacemaker (HCN) channels. Circulation. 2007 Apr. 10; 115(14):1839-50.
7. Choi Y-H, Stamm C, Hammer P E, Kwaku K F, Marler J J, Friehs I, Jones M, Rader C M, Roy N, Eddy M-T, Triedman J K, Walsh E P, McGowan F X, del Nido P J, Cowan D B. Cardiac conduction through engineered tissue. Am J Pathol. 2006 July; 169(1):72-85.
8. Mulpuru S K, Madhavan M, McLeod C J, Cha Y-M, Friedman P A. Cardiac Pacemakers: Function, Troubleshooting, and Management: Part 1 of a 2-Part Series. J Am Coll Cardiol. 2017 Jan. 17; 69(2):189-210.
9. McVenes R, Hansen N, Lahtinen S P, Stokes K. The salty dog: serum sodium and potassium effects on modern pacing electrodes. Pacing Clin Electrophysiol PACE. 2007 January; 30(1):4-11.
10. Lee R J, Sievers R E, Gallinghouse G J, Urseil P C. Development of a model of complete heart block in rats. J Appl Physiol Bethesda Md. 1985.1998 August; 85(2):758-63.
11. Dai W, Wold L E, Dow J S, Kloner R A. Thickening of the infarcted wall by collagen injection improves left ventricular function in rats: a novel approach to preserve cardiac function after myocardial infarction. J Am Coll Cardiol. 2005 Aug. 16; 46(4):714-9.

12. Ifkovits J L, Tous E, Minakawa M, Morita M, Robb J D, Koomalsingh K J, Gorman J H, Gorman R C, Burdick J A. Injectable hydrogel properties influence infarct expansion and extent of postinfarction left ventricular remodeling in an ovine model. *Proc Natl Acad Sci USA.* 2010 Jun. 22; 107(25): 11507-12.
13. Christman K L, Vardanian A J, Fang Q, Sievers R E, Fok H H, Lee R J. Injectable fibrin scaffold improves cell transplant survival, reduces infarct expansion, and induces neovasculature formation in ischemic myocardium. *J Am Coll Cardiol.* 2004 Aug. 4; 44(3):654-60.
14. MacCarter D J, Lundberg K M, Corstjens J P. Porous electrodes: concept, technology and results. *Pacing and clinical electrophysiology: PACE.* 1983; 6:427-435.
15. Herrlich S, Spieth S, Gerstmann H, et al. Drug release mechanisms of steroid eluting rings in cardiac pacemaker lead electrodes. *Conference proceedings: . . . Annual International Conference of the IEEE Engineering in Medicine and Biology Society. IEEE Engineering in Medicine and Biology Society. Annual Conference.* 2012; 2012:681-684.
16. Elmqvist H, Schueller H, Richter G. The carbon tip electrode. *Pacing and clinical electrophysiology: PACE.* 1983; 6:436-439.
17. MacCarter D J, Lundberg K M, Corstjens J P. Porous electrodes: concept, technology and results. *Pacing and clinical electrophysiology: PACE.* 1983; 6:427-435.
18. Herrlich S, Spieth S, Gerstmann H, et al. Drug release mechanisms of steroid eluting rings in cardiac pacemaker lead electrodes. *Conference proceedings: . . . Annual International Conference of the IEEE Engineering in Medicine and Biology Society. IEEE Engineering in Medicine and Biology Society. Annual Conference.* 2012; 2012:681-684.
19. Echave M C, Del Burgo L S, Pedraz J L, Orive G. Gelatin as Biomaterial for Tissue Engineering. *Current pharmaceutical design.* 2017.
20. Laughner J I, Ng F S, Sulkin M S, Arthur R M, Efimov I R. Processing and analysis of cardiac optical mapping data obtained with potentiometric dyes. *American journal of physiology. Heart and circulatory physiology.* 2012; 303: H 753-765.
21. Curtis, M. J. et al. The Lambeth Conventions (II): guidelines for the study of animal and human ventricular and supraventricular arrhythmias. Pharmacol. Ther. 139, 213-248 (2013).
22. Nguyen, T. et al. Postinfarction survival and inducibility of ventricular arrhythmias in the spontaneous hypertensive rat: effects of ramipril and hydralazine. Circulation 98, 2074-2080 (1998).
23. Ortega D F, Barja L D, Logarzo E, Mangani N, Paolucci A, Bonomini M R. Non-selective His bundle pacing with a biphasic waveform: enhancing septal resynchronization. *Europace.* 2017.
24. Mond H, Holley L, Hirshorn M. The high impedance dish electrode—clinical experience with a new tined lead. *Pacing and clinical electrophysiology: PACE.* 1982; 5:529-534.
25. Masini M, Lazzari M, Lorenzoni R, et al. Activated pyrolytic carbon tip pacing leads: an alternative to steroid-eluting pacing leads? *Pacing and clinical electrophysiology: PACE.* 1996; 19:1832-1835.
26. Frohlig G, Bolz A, Strobel J, et al. A fractally coated, 1.3 mm2 high impedance pacing electrode. *Pacing and clinical electrophysiology: PACE.* 1998; 21:1239-1246.
27. Crossley G H, Sorrentino R A, Exner D V, et al. Extraction of chronically implanted coronary sinus leads active fixation vs passive fixation leads. *Heart Rhythm.* 2016; 13:1253-1259.
28. Mond H G, Helland J R, Stokes K, Bornzin G A, McVenes R. The electrode-tissue interface: the revolutionary role of steroid-elution. *Pacing and clinical electrophysiology: PACE.* 2014; 37:1232-1249.
29. Netusil M. Small surface electrodes for cardiac pacing and their effect on the longevity of pacemakers. *Cor et vasa.* 1972; 20:121-128.
30. Sideris S, Drakopoulou M, Oikonomopoulos G, et al. Left Ventricular Pacing through Coronary Sinus Is Feasible and Safe for Patients with Prior Tricuspid Valve Intervention. *Pacing and clinical electrophysiology: PACE.* 2016; 39:378-381.
31. Furman S, Garvey J, Hurzeler P. Pulse duration variation and electrode size as factors in pacemaker longevity. *The Journal of thoracic and cardiovascular surgery.* 1975; 69:382-389.
32. Kubus P, Materna O, Gebauer R A, et al. Permanent epicardial pacing in children: long-term results and factors modifying outcome. *Europace.* 2012; 14:509-514.
33. Zhang H, Zhang X-S, Cheng X, et al. A flexible and implantable piezoelectric generator harvesting energy from the pulsation of ascending aorta: in vitro and in vivo studies. *Nano Energy.* 2015; 12:296-304.
34. Stokes K B, Bird T, Gunderson B. The mythology of threshold variations as a function of electrode surface area. *Pacing and clinical electrophysiology: PACE.* 1991; 14:1748-1751.

I claim:

1. A biocompatible conductive biomaterial comprising a conductive polymer and a biocompatible component, the conductive polymer comprising an aminomethoxybenzoic acid (AMBA) polymer, wherein the conductive polymer is covalently conjugated to the biocompatible component, wherein the conductivity of the biomaterial is greater than, at least or equal to about $10^{-6}$ S/cm and wherein the AMBA polymer consists of polymerized AMBA monomers.

2. The biocompatible conductive biomaterial of claim 1, wherein the AMBA monomer is selected from 3-amino-4-methoxybenzoic acid (3-4-AMBA), 4-amino-2-methoxybenzoic acid (4-2-AMBA), 4-amino-3-methoxybenzoic acid (4-3-AMBA), 2-amino-5-methoxybenzoic acid (2-5-AMBA), and 2-amino-4-methoxybenzoic acid (2-4-AMBA), and mixtures thereof.

3. The biocompatible conductive biomaterial of claim 1, wherein the biocompatible component is selected from gelatin, chitosan, collagen, fibronectin, elastin, alginate, and derivatives and mixtures thereof or wherein the biocompatible component comprises a synthetic product, optionally a biodegradable synthetic polymer.

4. The biocompatible conductive biomaterial of claim 3, wherein the biocompatible component is or comprises gelatin.

5. The biocompatible conductive biomaterial of claim 1, wherein the conductive polymer is covalently conjugated, to the biocompatible component.

6. The biocompatible conductive biomaterial of claim 1, wherein the biomaterial is a liquid solution, a hydrogel, a membrane, a 3D-patch or sponge, a sheet, or a mesh for grafting.

7. The biocompatible conductive biomaterial of claim 1, wherein the biomaterial is a hydrogel, optionally wherein the hydrogel is crosslinked.

8. The biocompatible conductive biomaterial of claim 1, wherein the biocompatible conductive biomaterial has a conductivity of at least or greater than about $10^{-5}$ S/cm, or of at least or greater than about $10^{-4}$ S/cm or least or greater than about $10^{-3}$ S/cm or least or greater than about $10^{-2}$ S/cm.

9. The biocompatible conductive biomaterial of claim 1, wherein the biocompatible conductive biomaterial has a conductivity of at least 2-fold, at least 3-fold, at least 4-fold, at least 5-fold, at least 6-fold, at least 7-fold, at least 8-fold, at least 9-fold, or at least 10-fold greater than a control biomaterial that does not comprise the conductive polymer.

10. The biocompatible conductive biomaterial of claim 1, wherein the molar ratio of the conductive polymer and the biocompatible component is about 30:1 to about 60:1.

11. The biocompatible conductive biomaterial of claim 1 further comprising one or more of culture media and cardiomyocytes.

12. A method of ameliorating or treating a heart condition, the method comprising: introducing a biocompatible conductive biomaterial to the heart of a subject in need thereof, wherein the biocompatible conductive biomaterial comprises a conductive polymer and a biocompatible component, the conductive polymer comprising an aminomethoxybenzoic acid (AMBA) polymer, wherein the conductive polymer is covalently conjugated to the biocompatible component, wherein the conductivity of the biomaterial is greater than, at least or equal to about $10^{-6}$ S/cm and wherein the AMBA polymer consists of polymerized AMBA monomers.

13. The method of claim 12, wherein the heart condition is myocardial infarction, ischemic myocardium, myocardial fibrosis, heart failure, atrioventricular block, arrhythmia, bradycardia or a conduction abnormality.

14. The method of claim 13, wherein the heart condition is atrioventricular block and the biocompatible conductive biomaterial is for restoring atrioventricular conduction.

15. The method of claim 13, wherein the heart condition is myocardial fibrosis and the biocompatible conductive biomaterial is introduced into or onto fibrotic scar tissue.

16. The method of claim 15 wherein the biocompatible conductive biomaterial is for reducing the occurrence of cardiac arrhythmia.

17. The method of claim 12, wherein the biocompatible conductive biomaterial is for reducing the pacing threshold of a cardiac pacemaker or for increasing myocardium reactivity to heart pacing in the subject.

18. The method of claim 14 wherein the heart condition results from cardiac surgery after replacing a cardiac valve.

* * * * *